(12) United States Patent
Assaraf et al.

(10) Patent No.: US 8,470,844 B2
(45) Date of Patent: Jun. 25, 2013

(54) IMIDAZOACRIDINONE DERIVATIVE COMPOUNDS AND METHODS FOR THEIR USE

(75) Inventors: Yehuda G. Assaraf, Doar-Na Misgav (IL); Eran E. Bram, Doar-Na Lev HaSharon (IL); Yamit Bney-Moshe, Haifa (IL); Andrzej M. Skladanowski, Gdansk (PL)

(73) Assignee: Technion Research & Development Foundation Limited, Haifa (IL)

( * ) Notice: Subject to any disclaimer, the term of this patent is extended or adjusted under 35 U.S.C. 154(b) by 405 days.

(21) Appl. No.: 12/585,252

(22) Filed: Sep. 10, 2009

(65) Prior Publication Data

US 2010/0137351 A1 Jun. 3, 2010

Related U.S. Application Data

(60) Provisional application No. 61/096,156, filed on Sep. 11, 2008.

(51) Int. Cl.
*A61K 31/4748* (2006.01)
*C07D 471/08* (2006.01)

(52) U.S. Cl.
USPC ............................................ 514/288; 546/66

(58) Field of Classification Search
USPC ............................................ 514/288; 546/66
See application file for complete search history.

(56) References Cited

U.S. PATENT DOCUMENTS 5,231,100 A * 7/1993 Cholody et al. ............... 514/288

FOREIGN PATENT DOCUMENTS
WO   WO 2008/016665 A2 * 2/2008

OTHER PUBLICATIONS

Cholody, W.M. et al.: Structure-Activity relationship for antineoplastic imidazoacridinones: Synthesis and antileukemic activity in vivo. J. Med. Chem., vol. 39, pp. 1028-1032, 1996.*
Alami et al. "Comparative Cytotoxicity of C-1311 in Colon Cancer In Vitro and In Vivo Using the Hollow Fiber Assay", Journal of Chemotherapy, 19(5): 546-553, 2007.
Al-Shawi et al. "Transition State Analysis of the Coupling of Drug Transport to ATP Hydrolysis by P-Glycoprotein", The Journal of Biological Chemistry, 278(52): 52629-52640, Dec. 26, 2003.
Assaraf "Molecular Basis of Antifolate Resistance", Cancer Metastasis Review, 26: 153-181, 2007.
Assaraf "The Role of Multidrug Resistance Efflux Transporters in Antifolate Resistance and Folate Homeostasis", Drug Resistance Updates, 9(4-5): 227-246, 2006.
Bates et al. "ABCG2 Mediates Differential Resistance to SN-38 (7-Ethyl-10-HydroxyCamptothecin) and Homocamptothecins", The Journal of Pharmacology and Experimental Therapeutics, JPET, 310(2): 836-842, 2004.
Belmont et al. "Acridine and Acridone Derivatives, Anticancer Properties and Synthetic Methods: Where Are We Now?" Anti-Cancer Agents in Medicinal Chemistry, 7(2): 139-169, 2007.
Borgnia et al. "Competition of Hydrophobic Peptides, Cytotoxic Drugs, and Chemosensitizers on A Common P-Glycoprotein Pharmacophore as Revealed by Its ATPase Activity", The Journal of Biological Chemistry, 271(6): 3163-3171, Feb. 9, 1996.
Borst et al. "Mammalian ABC Transporters in Health and Disease", Annual Reviews in Biochemistry, 71: 537-592, 2002.
Bram et al. "C421 Allele-Specific ABCG2 Gene Amplifications Confers Resistance to the Antitumor Triazoloacridone C-1305 in Human Lung Cancer Cells", Biochemical Pharmacology, 74: 41-53, 2007.
Bram et al. "Mutant Gly482 and Thr482 ABCG2 Mediate High-Level Resistance to Lipophilic Antifolates", Cancer Chemotherapy and Pharmacology, 58(6): 826-834, 2006.
Burger et al. "Preclinical Evaluation of Novel Imidazoacridinone Derivatives With Potent Activity Against Experimental Colorector Cancer", British Journal of Cancer, 74(9): 1369-1374, 1996.
Chau et al. "The Imidazoacridinone, C-1311 (Symadex™): the First of a Potent New Class of FLT3 Inhibitors", First AACR International Conference on Molecular Diagnostics in Cancer Therapeutic Development, 2 P., Sep. 2006.
Cholody et al. "5-[(Aminoalkyl)Amino]Imidazo[4,5,1-De]Acridin-6-Ones as a Novel Class of Antineoplastic Agents. Synthesis and Biological Activity", Journal of Medicinal Chemistry, 33(1): 49-52, 1990.
Clark et al. "Multiple Drugbinding Sites on the R482G Isoform of the ABCG2 Transporter", British Journal of Pharmacology, 149(5): 506-515, 2006.
Cooray et al. "Interaction of the Breast Cancer Resistance Protein With Plant Polyphenols", Biochemical and Biophysical Research Communications, 317: 269-275, 2004.
Deeley et al. "Transmembrane Transport of Endo- and Xenobiotics by Mammalian ATP-Binding Cassette Multidrug Resistance Proteins", Physiological Reviews, 86: 849-899, 2006.
Doyle et al. "Multidrug Resitance Mediated by the Breast Cancer Resistance Protein BCRP (ABCG2)", Oncogene, 22(47): 7340-7358, 2003.
Dzięgielewski et al. "Intercalation of Imidazoacridinones to DNA and Its Relevance to Cytotoxic and Antitumor Activity", Biochemical Pharmacology, 63: 1653-1662, 2002.
Ebert et al. "Identification of BCRP as Transporter of Benzo[α]Pyrene Conjugates Metabolically Formed in Caco-2 Cells and Its Induction by Ah-Receptor Agonists", Carcinogenesis, 26(10): 1754-1763, 2005.
Ebert et al. "Phytochemicals Induce Breast Cancer Resistance Protein in Caco-2 Cells and Enhance the Transport of Benzo[α]Pyrene-3-Sulfate", Toxicological Sciences, 96(2): 227-236, 2007.

(Continued)

Primary Examiner — Charanjit Aulakh

(57) ABSTRACT

The present invention provides IA derivative compounds of the formula:

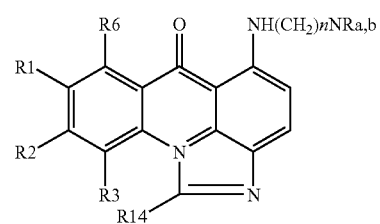

where the variables are described herein.

36 Claims, 8 Drawing Sheets
(2 of 8 Drawing Sheet(s) Filed in Color)

OTHER PUBLICATIONS

Eytan et al. "Functional Reconstruction of P-Glycoprotein Reveals An Apparant Near Stoichiometric Drug Transport to ATP Hydrolysis", The Journal of Biological Chemistry, 271(6): 3172-3178, Feb. 9, 1996.
Goodman et al. "Symadex™, A FLT3 Kinase Inhibitor, Is Metabolized by Aldehyde Oxidase", The FASEB Journal, 22: 920.5, 2008. Abstract.
Hyzy et al. "Antitumour Imidazoacridone C-1311 Induces Cell Death by Mitotic Catastrophe in Human Colon Carcinoma Cells", Biochemical Pharmacology, 69: 801-809, 2005.
Ifergan et al. "Cytoplasmic Confinement of Breast Cancer Resistance Protein (BCRP/ABCG2) as a Novel Mechanism of Adaption to Short-Term Folate Deprivation", Molecular Pharmacology, 67(4): 1349-1359, 2005.
Ifergan et al. "Folate Deprivation Results in the Loss of Breast Cancer Resistance Protein (BCRP/ABCG2) Expression", The Journal of Biological Chemistry, 279(24): 25527-25534, Jun. 11, 2004.
Jonker et al. "Breast Cancer Resistance Protein (Bcrp1/Abcg2) Is Expressed in the Harderian Gland and Mediates Transport of Conjugated Protoporphyrin IX", American Journal of Physiology—Cell Physiology, 292: C2204-C2212, Jun. 2007.
Jonker et al. "The Breast Cancer Resistance Protein Protects Against a Major Chlorophyll-Derived Dietary Phototoxin and Protoporphyria", Proc. Natl. Acad. Sci. USA, 99(24): 15649-15654, Nov. 26, 2002.
Krishnamurthy et al. "The Stem Cell Marker Bcrp/ABCG2 Enhances Hypoxic Cell Survival Through Interactions With Heme", The Journal of Biological Chemistry, 279(23): 24218-24225, Jun. 4, 2004.
Kuśnierczyk et al. "Experimental Antitumor Activity and Toxicity of the Selected Triazolo- and Imidazoacridinones", Archivum Immunologiae et Therapiae Experimentalis, 42: 415-423, 1994.
Mellor et al. "Resistance to Chemotherapy in Cancer: A Complex and Integrated Cellular Response", Pharmacology, 81(4): 275-300, 2008.
Mueller et al. "Occurrence of Emodin, Chrysophanol and Physcion in Vegetables, Herbs and Liqours. Genotoxicity and Anti-Genotoxicity of the Anthraquinones and the Whole Plants", Food and Chemical Toxicology, 37(5): 481-491, 1999.
Nakanishi et al. "Quantitative analysis of Breast Cancer Resistance Protein and Cellular Resistance to Flavopiridol in Acute Leukemia Patients", Clinical Cancer Research, 9(9): 3320-3328, Aug. 15, 2003.
Poindessous et al. "Marked Activity of Irofulven Toward Human Carcinoma Cells: Comparison With Cisplatin and Ecteinascidin", Clinical Cancer Research, 9(7): 2817-2825, Jul. 2003.
Polgar et al. "ABCG2: Structure, Function and Role in Drug Response", Expert Opinion on Drug Metabolism & Toxicology, 4(1): 1-15, 2008.
Rabindran et al. "Fumitremorgin C Reverses Multidrug Resistance in Cells Transfected With the Breast Cancer Resistance Protein", Cancer Research, 60: 47-50, Jan. 1, 2000.
Rajendra et al. "Differential Effects of the Breast Cancer Resistance Protein on the Cellular Accumulation and Cytotoxicity of 9-Aminocamptothecin and 9-Nitrocamptothecin", Cancer Research, 63(12): 3228-3233, Jun. 15, 2003.
Robey et al. "Mutations at Amino-Acid 482 in the ABCG2 Gene Affect Substrate and Antagonist Specificity", British Journal of Cancer, 89(10): 1971-1978, 2003.
Ross et al. "Expression of Breast Cancer Resistance Protein in Blast Cells From Patients With Acute Leukemia", Blood, 96(1): 365-368, Jul. 1, 2000.
Shafran et al. "ABCG2 Harboring the Gly482 Mutation Confers High-Level Resistance to Various Hydrophilic Antifolates", Cancer Research, 65(18): 8414-8422, Sep. 15, 2005.
Sharom "ABC Multidrug Transporters: Structure, Function and Role in Chemoresistance", Pharmacogenomics, 9(1): 105-127, 2008.
Skladanowski et al. "Inhibition of DNA Topoisomerase II by Imidazoacridinones, New Antineoplstic Agents With Strong Activity Against Solid Tumors", Molecular Pharmacology, 49(5): 772-780, 1996.
Steinbach et al. "BCRP Gene Expression Is Associated With a Poor Response to Remission Induction Therapy in Childhood Acute Myeloid Leukemia", Leukemia, 16: 1443-1447, 2002.
Szakács et al. "Targeting Multidrug Resistance in Cancer", Nature Reviews: Drug Discovery, 5(3): 219-234, Mar. 2006.
Takagi et al. "Novel E-Ring Camptothecin Keto Analogues (S38809 and S39625) Are Stable, Potent, and Selective Topoisomerase I Inhibitors Without Being Substrates of Drug Efflux Transporters", Molecualr Cancer Therapeutics, 6(12): 3229-3238, Dec. 2007.
Topcu DNA Topoisomerases as Targets for Anticancer Drugs, Journal of Clinical Pharmacy and Therapeutics, 26: 405-416, 2001.
Turner et la. "ABCG2 Expression, Function, and Promoter Methylation in Human Multiple Myeloma", Blood, 108(12): 3881-3889, Dec. 1, 2006.
Van den Heuvel-Eibrink et al. "Increased Expression of the Breast Cancer Resistance Protein (BCRP) in Relapsed or Refractory Acute Myeloid Leukemia (AML)", Leukemia, 16: 833-839, 2002.
Van Herwaarden et al. "Multidrug Transporter ABCG2/Breast Cancer Resistance Protein Secretes Riboflavin (Vitamin B2) Into Milk", Molecular and Cellular Biology, 27(4): 1247-1253, Feb. 2007.
Velamakanni et al. "A Functional Steroid-Binding Element in an ATP-Binding Cassette Multidrug Transporter", Molecular Pharmacology, 73(1): 12-17, 2008.
Wang "Extending the Good Diet, Good Health Paradigm: Modulation of Breast Cancer Resistance Protein (BCRP) by Flavonoids", Toxicological Sciences, 96(2): 203-205, 2007.
Yoshikawa et al. "Novel Camptothecin Analogues That Circumvent ABCG2-Associated Drug Resistance in Human Tumor Cells", International Journal of Cancer, 110(6): 921-927, 2004.
Dzię gielewski et al. "Intercalation of Imidazoacridinones to DNA and Its Relevance to Cytotoxic and Antitumor Activity", Biochemical Pharmacology, 63: 1653-1662, 2002.
Jonker et al. "Breast Cancer Resistance Protein (Bcrpl/Abcg2) Is Expressed in the Harderian Gland and Mediates Transport of Conjugated Protoporphyrin IX", Americna Journal of Physiology—Cell Physiology, 292: C2204-C2212, Jun. 2007.

* cited by examiner

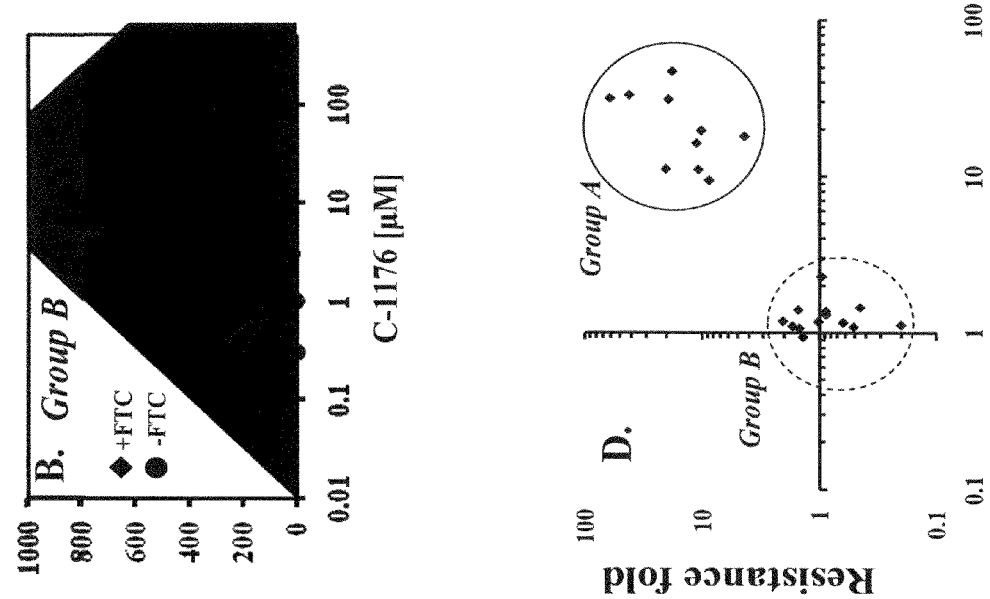
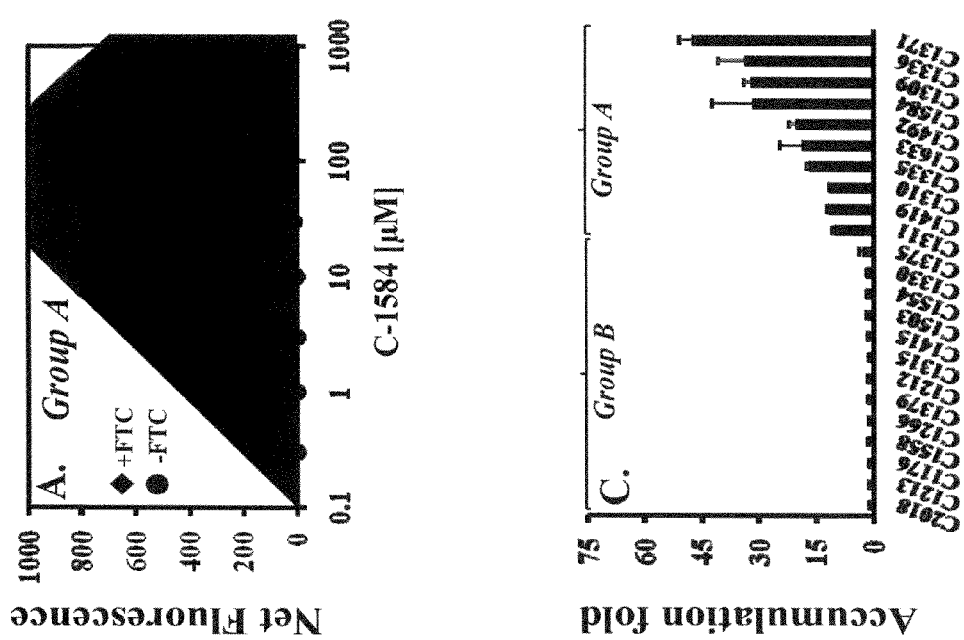
Fig. 3

IMIDAZOACRIDINONE DERIVATIVE COMPOUNDS AND METHODS FOR THEIR USE

RELATED APPLICATIONS

This application claims the benefit of priority of U.S. Provisional Patent application No. 61/096,156, filed on Sep. 11, 2008, the contents of which are incorporated herein by reference.

FIELD OF THE INVENTION

The present invention relates to imidazoacridinone (IA) derivative compounds. More particularly, the present invention relates to the structural determinants of IA derivative compounds that facilitate antitumor cytotoxicity.

INTRODUCTION

Cancer is a major cause of mortality worldwide. Despite advancements in diagnosis and treatment, there remains a great need for novel methods of treating cancer and for identifying novel agents that inhibit cancer cells.

More specifically, the frequent emergence of anticancer drug resistance phenomena continues to be a major impediment towards curative chemotherapy of various human malignancies. In this respect, multidrug resistance (MDR) is perhaps the most extensively studied major mechanism of anticancer drug resistance. MDR is mediated by members of the ATP-binding cassette superfamily of transporters including ABCB1 (P-glycoprotein), ABCC1 (MRP1) and ABCG2 (BCRP). Borst, P., and Elferink, R. O. (2002) *Annu Rev Biochem* 71, 537-592; Deeley, R. G., et al., (2006) *Physiol Rev* 86(3), 849-899; Polgar, O., et al., (2008) *Expert Opin Drug Metab Toxicol* 4(1), 1-15. Recognizing a plethora of hydrophobic, hydrophilic and amphiphilic cytotoxic substrates, these ATP-driven efflux pumps extrude out of malignant tumors, structurally distinct endo- and xenobiotics, many of which are key antitumor agents thereby resulting in a wide spectrum drug resistance.

Recent studies have shown that increased expression of ABCG2 prior to chemotherapy may underlie inherent tumor drug resistance including the treatment of acute myeloid leukemia (AML) with established ABCG2 substrates such as mitoxantrone, topotecan and doxorubicin. In this respect, using RT-PCR to determine ABCG2 transcript levels in blast cells obtained from AML patients, high levels of ABCG2 were detected in about a third of the patients. Ross, D. D., et al. (2000) *Blood* 96(1), 365-368. Subsequent studies observed a tight correlation between ABCG2 mRNA levels and the viability of acute leukemia blast cells in the presence of the cyclin-dependent kinase inhibitor, flavopiridol. Nakanishi, T., et al., (2003) *Clin Cancer Res* 9(9), 3320-3328.

Hence, ABCG2-dependent MDR may lead to incomplete eradication of leukemic cells thereby resulting in clonal expansion and relapse of the chemo-resistant disease. This is in accord with recent observations that ABCG2 mRNA levels were significantly increased in relapsed AML. Steinbach, D., et al., (2002) *Leukemia* 16(8), 1443-1447; van den Heuvel-Eibrink, M. M., et al., P. (2002) *Leukemia* 16(5), 833-839. Hence, identification of novel modalities and strategies that overcome ABCG2-dependent MDR phenomena in various human cancers is one of the major goals of current preclinical cancer therapeutics.

Symadex is the lead compound of a novel class of imidazoacridinone (IA) derivative compounds, which are currently undergoing phase II clinical trials for the treatment of various cancers. Problematically, Symadex is extruded by ABCG2-overexpressing lung cancer A549/K1.5 cells, thereby resulting in a marked drug resistance. The present invention addresses this problem and provides additional benefits as well.

SUMMARY OF THE INVENTION

The present invention provides IA derivative compounds of the formula:

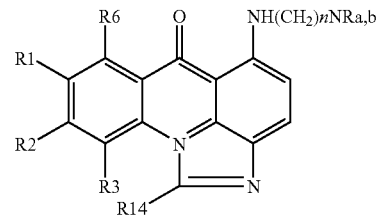

where the variable are described below.

Also provided are methods of testing such compounds for activity against cancer or an autoimmune condition, as well as methods of improving the status of a subject with such condition.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows the general structural formula of IA derivatives (designated "IA structure"), as well as the specific structure of two such derivatives (designated "C1311" and "C1305"). The remaining structures in FIGS. 1A and 1B are various polycyclic chemotherapeutic compounds. Substrates for the transporter protein ABCG2 containing a putative hydrogen bond donor (designated in red) for ABCG2 interaction (FIG. 1A), and similar polycyclic drugs reported as non-ABCG2 substrates lacking the positional hydrogen bond donor group are shown in FIG. 1B.

FIGS. 3A-3D show the comparative exclusion of IA derivative compounds from A549/K1.5 cells in the presence or absence of fumitremorgin C (FTC). A549/K1.5 cells were suspended in a 20 nM HEPES (pH 7.3)-buffered medium containing increasing concentrations of the various IA derivatives ranging from 0.01 µM to 200 µM and incubated for 1 hr at 37° C. both in the presence or absence of 5 µM fumitremorgin C. Average net fluorescence at the various concentrations of Group A derivatives representative IA C-1584 (A) or Group B representative IA C-1176 (B) from at least 3 separate experiments are shown±S.D. (C) Quantitative comparison of FTC inducible IA accumulation fold (AF) at an equal [10 µM] concentration. Results depicted are means±S.D obtained from the above 3 independent experiments. (D) Clustering of the various IAs on an RF vs. AF dot plot.

DETAILED DESCRIPTION OF THE INVENTION

Figure 1:
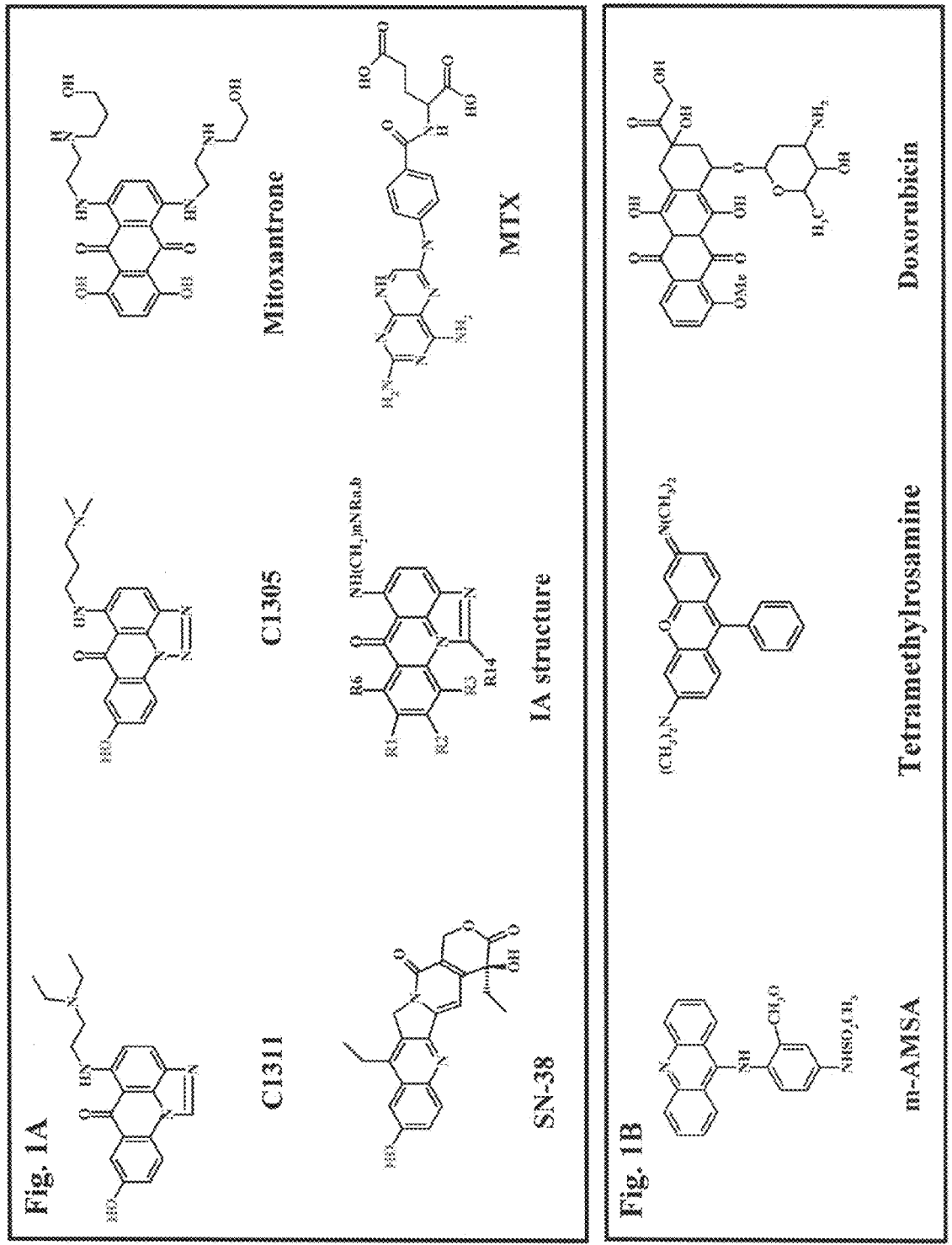
FIGS. 1A-1B.

The present invention relates to compounds, methods of testing such compounds for activity against cancer or an autoimmune condition, and methods of treating a subject with such conditions with such compounds. The compounds have the formula:

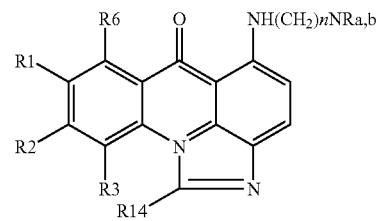

where R1, R2, R3 and R6 are hydrogen, halogen, hydroxy, $C_1$ to $C_6$ alkyl, $C_1$ to $C_6$ substituted alkyl, oxo, amino, protected amino, (monosubstituted)amino, (disubstituted) amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano or thiol;

R14, Ra and Rb are hydrogen, $C_1$ to $C_{12}$ alkyl or $C_1$ to $C_{12}$ substituted alkyl; and n is 1 to 30.

In a preferred embodiment none of R1, R2 and R3 is hydroxyl. In another preferred embodiment, n is greater than 5 and, more preferably, greater than 6. In an additional preferred embodiment, Ra and Rb together include more than 5 carbon atoms. In yet another preferred embodiment, if a) n is less than 6; or b) Ra and Rb together include less than 5 carbon atoms, then c) none of R1, R2 and R3 is hydroxyl.

In another preferred embodiment, R1, R2, R3 and R6 are, hydrogen, hydroxy, $C_1$ to $C_6$ alkyl or $C_1$ to $C_6$ alkoxy. Also preferred is where R1, R2 and R3 are hydrogen, hydroxy, $C_1$ to $C_3$ alkyl or methoxy.

In an additional embodiment, R6 is hydrogen or methoxy. Another embodiment proved where R14, Ra and Rb are hydrogen or $C_1$ to $C_3$ alkyl.

The methods of the invention include those against cancer. Preferred cancers include breast cancer, particularly metastatic breast cancer, lung cancer, particularly non-small cell, and colorectal cancer.

The methods of the invention include those against autoimmune conditions. Such preferred conditions include multiple sclerosis and arthritis, particularly rheumatoid arthritis.

The present invention centers on Symadex (designated a "C1311 in FIG. 1A and Table I), which is the lead compound of a novel class of IA derivatives currently undergoing phase II clinical trials for the treatment of various cancers. Symadex appears to interact with ABGC2, a transporter protein and, as a result, extruded from target cancer cells.

The present invention identifies the IA residues essential for recognition by ABCG2 by examining the ability of ABCG2 to extrude and confer resistance to 23 IA derivatives listed in Table I below. These derivatives differ solely at defined residue(s) revolving their common core, fused four-ring structure.

Taking advantage of the fluorescent characteristics of IA derivative compounds, ABCG2-dependent efflux and drug resistance was determined in A549/K1.5 cells using flow cytometric analysis in the presence or absence of fumitremorgin C, an ABCG2 transport inhibitor.

Based on these findings, a hydroxyl group at one of the R1-R3 positions in the above-depicted formula is essential for ABCG2-mediated efflux and IA derivative resistance. In addition, elongation of the common distal aliphatic side chain (—NH(CH$_2$)nNRa,Rb) attenuates ABCG2-dependent efflux thereby resulting in retention of parental cell sensitivity.

Figure 6:
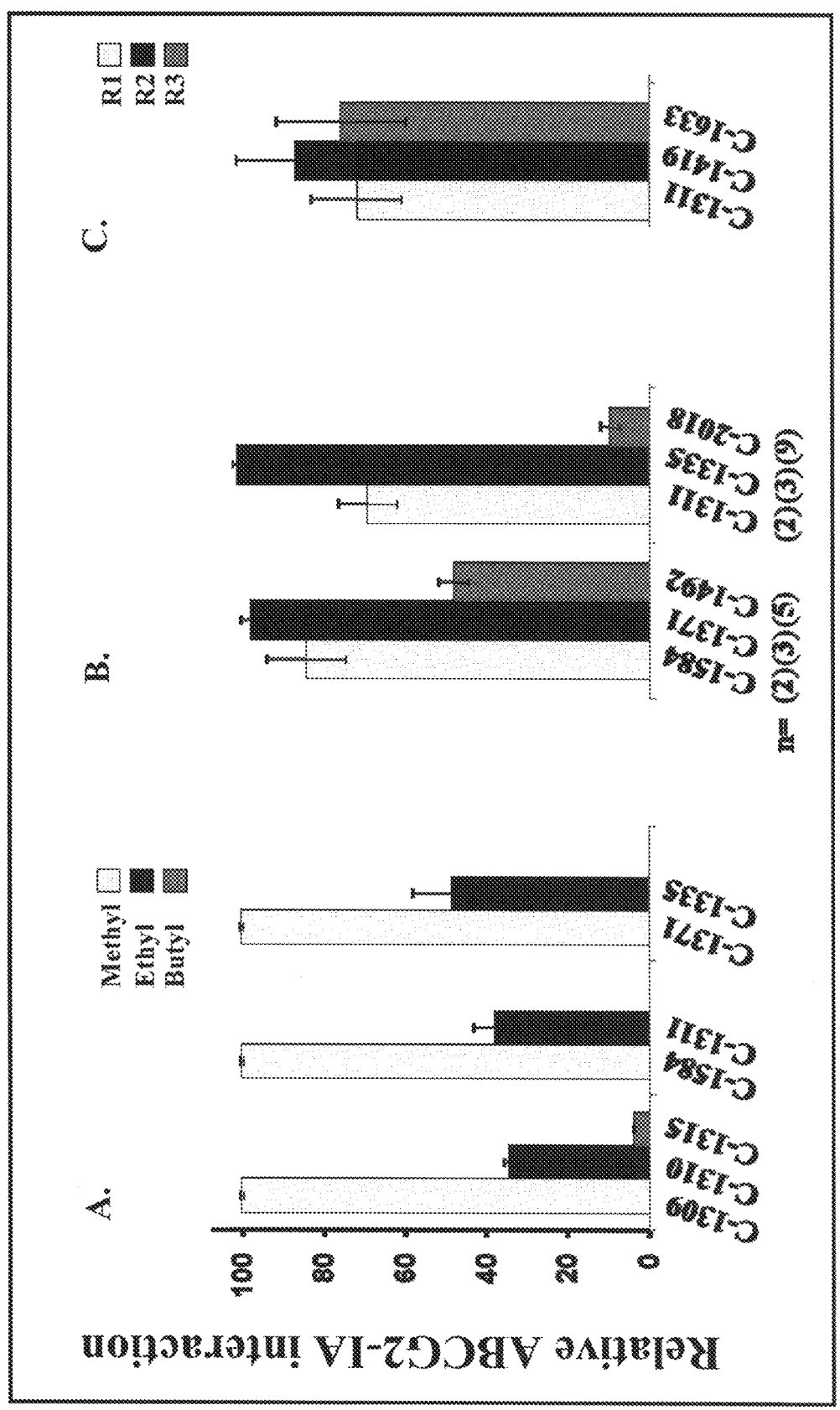
FIGS. 6A-6C show the structural determinants in the IA derivative side chain effecting ABCG2-IA interaction. The effects of Ra,b size (A), n length (B) and OH-position around the outer ring (C) on ABCG2-IA interaction were evaluated. IA derivatives were divided into comparable subsets, differing within subsets only by the parameter evaluated. Relative ABCG2-IA interaction was assessed using the integrated RF and AF values±S.E, as specified below.

Thus, IA derivative compounds a) without OH at R1-R3; and/or b) with a longer side chain (n greater than 5 and/or Ra plus Rb including more than 4 carbon atoms) results in a more effective compound for improving the conditions described herein. See FIG. 6.

As discussed above, Symadex (shown in FIG. 1A and Table I as "C-1311") is the lead compound in clinical development from a novel series of cytotoxic agents, IA derivative compounds. Cholody, W. M., et al., (1990) J Med Chem 33(1), 49-52; Cholody, W. M., et al., (1990) J Med Chem 33(10), 2852-2856; Kusnierczyk, H., et al., (1994) Arch Immunol Ther Exp (Warsz) 42(5-6), 415-423; Burger, A. M., et al., (1996) Br J Cancer 74(9), 1369-1374; Dziegielewski, J., et al., (2002) Biochem Pharmacol 63(9), 1653-1662; Hyzy, M., et al., (2005) Biochem Pharmacol 69(5), 801-809; and Skladanowski, A., et al., (1996) Mol Pharmacol 49(5), 772-780. Symadex has shown preclinical activity as a potent and selective FLT3 receptor tyrosine kinase inhibitor Goodman, K., et al., (2008) FASEB J. 22(1_MeetingAbstracts), 920-925; Chau, M., et al., (2006) The imidazoacridinone, C-1311 (Symadex™): The first of a potent new class of FLT3 inhibitors. In. *AACR 97th annual meeting*.

Specifically, Symadex is currently undergoing Phase II clinical trials as a novel anticancer drug in oncology indications including colorectal cancer Alami, N., et al., (2007) *J Chemother* 19(5), 546-553. Moreover, Symadex is also explored for the treatment of non-neoplastic disorders such as autoimmune diseases, including multiple sclerosis and rheumatoid arthritis, where early preclinical data have shown promising pharmacological activity.

Since IA derivative compounds share common structural features with various chemotherapeutic drugs and naturally occurring bio-active compounds, The present invention identifies key structural determinants of IA derivative compounds that are crucial for substrate recognition and efflux by ABCG2. This identification is based on the markedly decreased accumulation of IA derivatives that contain a hydroxyl group at one of the positions R1, R2 or R3 in ABCG2-overexpressing A549/K1.5 cells using a flow cytometric assay that takes advantage of the inherent fluorescent properties of IAs. Consistently, restoration of cellular accumulation of hydroxyl group-containing IAs was achieved by co-incubation with the specific ABCG2 transport inhibitor, FTC. See FIG. 3. In contrast, IA derivative compounds devoid of a hydroxyl group at the R1-R3 positions accumulated to high levels in A549/K1.5 cells, irrespective of ABCG2 expression.

Figure 4:
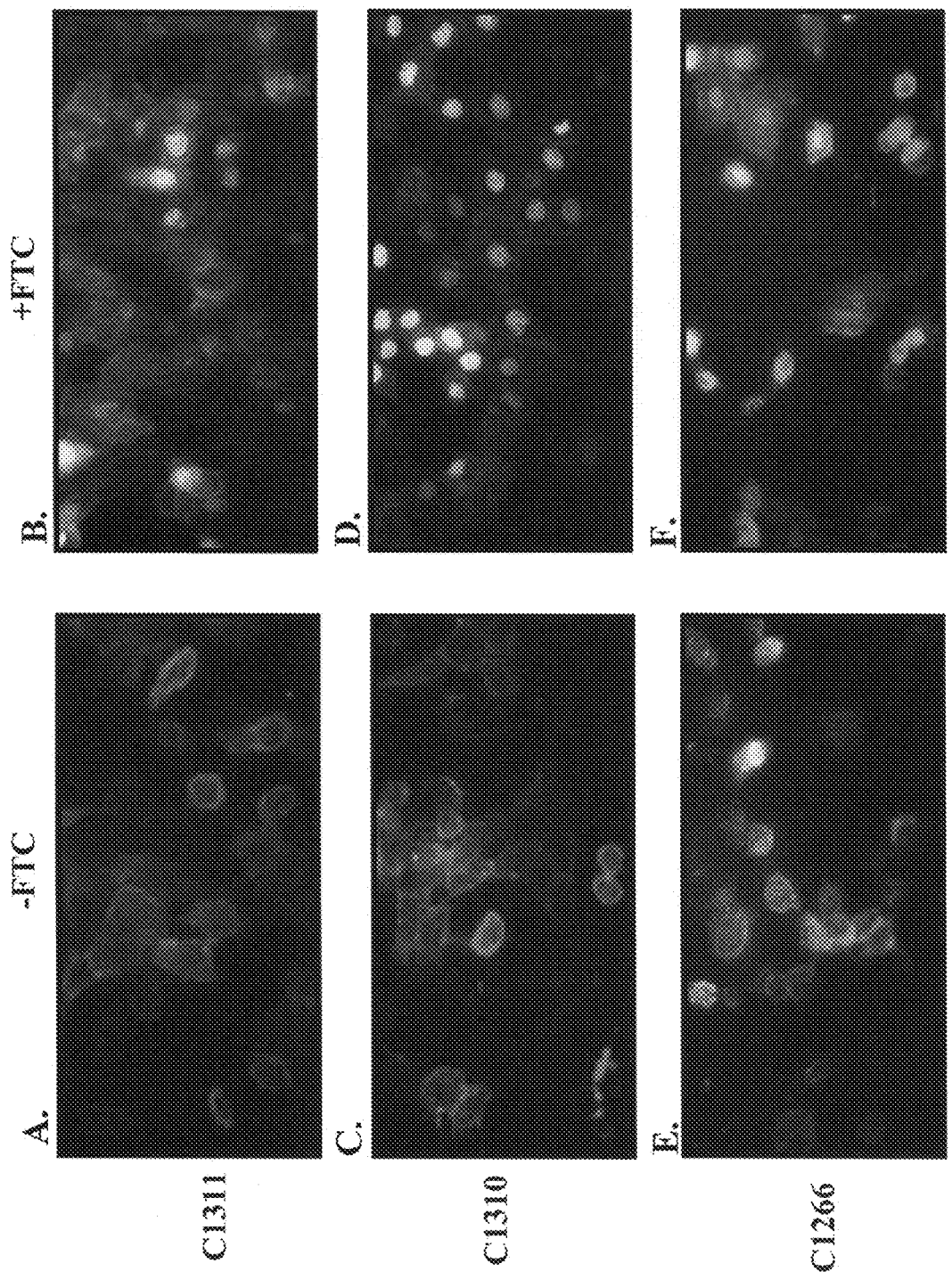
FIGS. 4A-4F show functionally over-expressed ABCG2 in A549/K1.5 cells, as revealed by surface 5D3 antibody immunofluorescence and fluorescent nuclear accumulation of selected Group A and B IA derivatives. Mono-layer growing A549/K1.5 cells were incubated for 1 hr at 37° C. with 10 µM of selected Group A derivatives: C-1311 (A, B), C-1310 (C, D) or the group B IA derivative C-1266 (E, F), in the presence (right column) or absence (left column) of 5 µM fumitremorgin C. Live cells were then subjected to immuno-labeling using a phycoerythrin-conjugated 5D3 antibody against ABCG2 and examined by immunofluorescence (IF) microscopy.

Secondly, fluorescence microscopy revealed that, while nuclei of parental A549 cells stained brightly with all IA derivative compounds, ABCG2-overexpressing A549/K1.5 cells failed to stain with hydroxyl group-containing IA derivative compounds, but stained intensely with hydroxyl group-lacking IA derivative compounds. See FIG. 4. Thirdly, A549/K1.5 cells displayed marked levels of drug resistance to hydroxyl group-containing IAs but retained parental cell sensitivity to IA derivative compounds lacking hydroxyl group at the R1-R3 positions. See FIG. 2. Finally, human embryonic kidney HEK293 cells stably transfected with the wild type ABCG2 (R482) or mutant G/T482 cDNAs displayed an excellent extrusion of hydroxyl containing IA derivative compounds. By contrast, FTC fully restored drug accumulation thereby establishing that both wild type and mutant ABCG2 mediates the efflux of these IA derivative compounds from ABCG2-overexpressing cells. See FIG. 8.

IA derivative compounds displayed differential levels of drug accumulation (up to 47-fold difference) and drug resistance (up to 61-fold), in ABCG2-overexpressing A549/K1.5 cells, as assessed by flow cytometry and cytotoxicity assays. This differential interaction with ABCG2 separated IA derivative compounds into two distinct groups—transport substrates (group A) and non-substrates of ABCG2 (group B). This cluster-like functional differentiation of IA derivative compounds depends on two basic IA structural features: a) The presence or absence of a hydroxyl group at one of the R1, R2 or R3 positions of the depicted fromula; or b) The linear and/or branched length of the IA distal side chain tail. Whereas the presence or absence of the facilitating hydroxyl group has an all-or-none impact on whether or not ABCG2 interacts with an IA derivative compound, the inhibitory effect that the IA tail length has on the ability of ABCG2 to recognize it as transport substrates is more gradual. Elongation of the aliphatic side chain tail (n) appears to produce a relatively moderate interference in the interaction of IA with ABCG2, which becomes significant only when the IA derivative compound contains a relatively longer side chain tails (n≧5). In contrast, modest elongations of the branched Ra,b tail group have a marked effect on the ability of ABCG2 to recognize and extrude IA derivative compounds, possibly due to the branched nature of the Ra,b group, leading to the simultaneous elongation of the dual tails thereby markedly contributing to increased bulk of the IA derivative compound. Hence, elongation of the IA tail appears to disrupt the optimal bulk fit of the compound into the putative ABCG2 pharmacophore, thereby precluding drug recognition and subsequent efflux.

As disclosed above, the most prominent feature of IA derivative compounds from group A of ABCG2 transport substrates was the presence of a hydroxyl group at one of the R1, R2 or R3 positions. These positions are located at the outskirts of the IA molecule and are, therefore, readily accessible to direct interaction with their environment, most likely as hydrogen bond donors. In this respect, a recent study on the nature of ABCG2 interaction with camptothecin analogues has revealed a similar dependence on the presence of similar hydroxyl or amine groups on the outer ring of the common camptothecin structure which proved to facilitate hydrogen bond formation essential for substrate recognition and efflux via ABCG2; these camptothecin positions are analogous to the present R1-R3 positions of IA derivative compounds. Yoshikawa, M., et al., (2004) *Int J Cancer* 110(6), 921-927. Indeed, ABCG2-dependent resistance to novel camptothecin analogues also obeys this general hydrogen bond rule. Rajendra, R., et al., (2003) *Cancer Res* 63(12), 3228-3233; Takagi, K., et al., (2007) *Mol Cancer Ther* 6(12 Pt 1), 3229-3238. These cumulative results emphasize the common and basic structural features of ABCG2 efflux substrates from different groups of polyaromatic cytotoxic agents.

Furthermore, a close inspection of known ABCG2 substrates such as SN-38, mitoxantrone and methotrexate reveals a distinct candidate for putative hydrogen-bond formation at a corresponding position of their polycyclic ring (FIG. 1, see group in red). Accordingly, non-substrates of ABCG2 with similar polycyclic structure lack the corresponding putative group facilitating hydrogen-bond formation (FIG. 1). An important functional implication of the essential role that putative hydrogen bond formation between ABCG2 and its substrates plays in endo- and xenobiotics extrusion relates to the transport capacity of ABCG2 and other MDR efflux transporters. It is established that MDR transporters of the ABC superfamily including ABCB1, ABCC1 as well as ABCG2 are relatively low affinity yet high capacity drug efflux transporters. For example, ABCG2 and ABCC1 through ABCC5 display affinities in the millimolar range for their transport substrate methotrextae, whereas their basal ATPase activity is in the range of 1-5 μmol/(minxmg) of protein. Assaraf, Y. G. (2006) *Drug Resist Updat* 9(4-5), 227-246; Assaraf, Y. G. (2007) *Cancer Metastasis Rev* 26(1), 153-181. Similarly, ABCB1 also exhibits an affinity in the millimolar range for various hydrophobic cytotoxic agents. Borgnia, M. J., Eytan, G. D., and Assaraf, Y. G. (1996) *J Biol Chem* 271(6), 3163-3171. Moreover, transport capacity reflected in the turnover number of substrates extruded per unit of time in MDR efflux transporters including ABCB1 has been found to be approximately 900 molecules/min. Eytan, G. D., Regev, R., and Assaraf, Y. G. (1996) *J Biol Chem* 271(6), 3172-3178.

A MDR efflux transporter that interacts with its drug substrates via low affinity interaction and transient binding through relatively weak hydrogen bonds facilitates the high capacity extrusion as opposed to high affinity transporters that may have lower turnover rates Al-Shawi, M. K., Polar, M. K., Omote, H., and Figler, R. A. (2003) *J Biol Chem* 278(52), 52629-52640.

IA derivative compound cytotoxicity can depend on the presence of a hydroxyl group at position R1 as well as a short IA tail. IA derivative compounds possessing both of these features maintained up to two orders of magnitude increased cytotoxicity towards ABCG2-lacking A549 lung cancer cells. The ability of ABCG2 to cope with a wide array of hydroxyl group-bearing bio-active molecules depends on its capacity to interact with alternative positions of the hydroxyl group, as with mitoxantrone and camptothecin analogues (FIG. 1). Accordingly, although the overall cytotoxicity of IA derivative compounds is markedly attenuated by alternative hydroxylation of IAs at the R2 or R3 positions, this change does not seem to significantly alter ABCG2 mediated IA efflux and drug resistance.

A549/K1.5 cells which displayed a marked ABCG2-dependent MDR phenotype to group A IA derivative compounds, were up to 5-fold more sensitive to hydroxyl group-lacking IA derivative compounds, including C-1266.

The term "$C_1$ to $C_{12}$ alkyl" denotes such radicals as methyl, ethyl, n-propyl, isopropyl, n-butyl, iso-butyl, sec-butyl, tert-butyl, amyl, tert-amyl, hexyl, heptyl, octyl, nonyl, decyl, undecyl, dodecyl and the like. Preferred "$C_1$ to $C_{12}$ alkyl" groups are methyl, ethyl, iso-butyl, sec-butyl and iso-propyl. Similarly, the term "$C_1$ to $C_{12}$ alkylene" denotes radicals of 1 to 12 carbons connected to two other parts in the compound.

The term "$C_2$ to $C_{12}$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, (as well as octenyl, nonenyl, decenyl, undecenyl, dodecenyl radicals attached at any appropriate carbon position and the like) as well as dienes and trienes of straight and branched chains.

The term "$C_2$ to $C_{12}$ alkynyl" denotes such radicals as ethanol, propynyl, 2-butynyl, 2-pentynyl, 3-pentynyl, 2-hexynyl, 3-hexynyl, 4-hexynyl, 2-heptynyl, 3-heptynyl, 4-heptynyl, 5-heptynyl (as well as octynyl, nonynyl, decynyl, undecynyl, dodecynyl radicals attached at any appropriate carbon position and the like) as well as di- and tri-ynes of straight and branched chains.

The terms "$C_1$ to $C_{12}$ substituted alkyl," "$C_2$ to $C_{12}$ substituted alkenyl," "$C_2$ to $C_{12}$ substituted alkynyl," "$C_1$ to $C_{12}$ substituted alkylene," "$C_2$ to $C_{12}$ substituted alkenylene" and "$C_2$ to $C_{12}$ substituted alkynylene" denote groups are substituted by one or more, and preferably one or two, halogen, hydroxy, protected hydroxy, oxo, protected oxo, $C_3$ to $C_7$ cycloalkyl, phenyl, naphthyl, amino, protected amino, (monosubstituted)amino, protected (monosubstituted) amino, (disubstituted)amino, guanidino, protected guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_{12}$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_{12}$ substituted alkoxy" means the alkyl portion of the alkoxy can be substituted in the same manner as in relation to $C_1$ to $C_{12}$ substituted alkyl. Similarly, the term "$C_1$ to $C_{12}$ phenylalkoxy" as used herein means "$C_1$ to $C_{12}$ alkoxy" bonded to a phenyl radical.

The term "$C_1$ to $C_{12}$ acyloxy" denotes herein groups such as formyloxy, acetoxy, propionyloxy, butyryloxy, pivaloyloxy, pentanoyloxy, hexanoyloxy, heptanoyloxy, octanoyloxy, nonanoyloxy, decanoyloxy, undecanoyloxy, dodecanoyloxy and the like.

Similarly, the term "$C_1$ to $C_{12}$ acyl" encompasses groups such as formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Preferred acyl groups are acetyl and benzoyl.

The term "$C_1$ to $C_{12}$ substituted acyl" denotes the acyl group substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, $C_1$ to $C_{12}$ alkyl ester, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted acyl groups may be substituted once or more, and preferably once or twice, with the same or with different substituents.

Examples of $C_1$ to $C_{12}$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

The substituent term "$C_3$ to $C_7$ cycloalkyl" includes the cyclopropyl, cyclobutyl, cyclopentyl, cyclohexyl or cycloheptyl rings. Similarly, a substituent that can be $C_3$ to $C_7$ cycloalkyl" can also be "$C_5$ to $C_7$ cycloalkyl," which includes the cyclopentyl, cyclohexyl or cycloheptyl rings.

The substituent term "$C_3$ to $C_7$ substituted cycloalkyl" or "$C_5$ to $C_7$ substituted cycloalkyl" indicates the above cycloalkyl rings substituted by one or two halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino groups.

The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_5$ to $C_7$ cycloalkenyl" denotes the above $C_5$ to $C_7$ cycloalkenyl rings substituted by a $C_1$ to $C_{12}$ alkyl radical, halogen, hydroxy, protected hydroxy, $C_1$ to $C_{12}$ alkoxy, trifluoromethyl, carboxy, protected carboxy, oxo, protected oxo, (monosubstituted)amino, protected (monosubstituted)amino, (disubstituted)amino, phenyl, substituted phenyl, amino, or protected amino.

The term "$C_5$ to $C_7$ cycloalkenylene" is a cycloalkenyl ring, as defined above, where the cycloalkenyl radical is bonded at two positions connecting together two separate additional groups. Examples of $C_5$ to $C_7$ cycloalkenylenes include 1,3-cyclopentylene and 1,2-cyclohexylene.

Similarly, the term "substituted $C_5$ to $C_7$ cycloalkenylene" means a cycloalkenylene further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group. Examples of substituted $C_5$ to $C_7$ cycloalkenylenes include 4-chloro-1,3-cyclopentylene and 4-methyl-1,2-cyclohexylene.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophen-yl, hexylmethyleneimino and heptylmethyleneimino.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl) carboxamide, trifluoromethyl, N—(($C_1$ to $C_{12}$ alkyl)sulfonyl) amino, N-(phenylsulfonyl)amino, heterocycle or substituted heterocycle groups.

The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furan, oxazolo, isoxazolo, phthalimido, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl) carboxamide, trifluoromethyl, N—(($C_1$ to $C_{12}$ alkyl)sulfonyl) amino or N-(phenylsulfonyl)amino groups.

The term "$C_7$ to $C_{18}$ phenylalkyl" denotes a $C_1$ to $C_{12}$ alkyl group substituted at any position within the alkyl chain by a phenyl. The definition includes groups of the formula: -phenyl-alkyl, -alkyl-phenyl and -alkyl-phenyl-alkyl. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{18}$ phenylalkyl groups are any one of the preferred alkyl groups described herein combined with a phenyl group.

Similarly, the term "$C_1$ to $C_{12}$ heterocycloalkyl" denotes a $C_1$ to $C_{12}$ alkyl group substituted at any position within the alkyl chain by a "heterocycle," as defined herein. The definition includes groups of the formula: -heterocyclic-alkyl, -alkyl-heterocyclic and -alkyl-heterocyclic-alkyl. Examples of such a group include 2-pyridylethyl, 3-piperydyl(n-propyl), 4-furylhexyl, 3-piperazyl(n-amyl), 3-morpholyl(sec-butyl) and the like. Preferred $C_1$ to $C_{12}$ heterocycloalkyl groups are any one of the preferred alkyl groups described herein combined with any one of the preferred heterocycle groups described herein.

The terms "$C_7$ to $C_{18}$ substituted phenylalkyl" and "$C_1$ to $C_{12}$ substituted heterocycloalkyl" denote a $C_7$ to $C_{18}$ phenylalkyl group or $C_1$ to $C_{12}$ heterocycloalkyl substituted (on the alkyl or, where applicable, phenyl or heterocyclic portion) with one or more, and preferably one or two, groups chosen from halogen, hydroxy, protected hydroxy, oxo, protected oxo, amino, protected amino, (monosubstituted)amino, protected (monosubstituted)amino, (disubstituted)amino, guanidino, protected guanidino, heterocyclic ring, substituted heterocyclic ring, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N—($C_1$ to $C_{12}$ dialkyl)carboxamide, cyano, N—($C_1$ to $C_{12}$ alkylsulfonyl)amino, thiol, $C_1$ to $C_{10}$ alkylthio, $C_1$ to $C_{10}$ alkylsulfonyl groups; and/or the phenyl group may be substituted with one or more, and preferably one or two, substituents chosen from halogen, hydroxy, protected hydroxy, cyano, nitro, $C_1$ to $C_{12}$ alkyl, $C_1$ to $C_{12}$ substituted alkyl, $C_1$ to $C_{12}$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino, N-(phenylsulfonyl)amino, cyclic $C_2$ to $C_{12}$ alkylene or a phenyl group, substituted or unsubstituted, for a resulting biphenyl group. The substituted alkyl, phenyl or heterocyclic groups may be substituted with one or more, and preferably one or two, substituents which can be the same or different.

Examples of the term "$C_7$ to $C_{18}$ substituted phenylalkyl" include groups such as 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 544-aminomethylphenyl)-3-(aminomethyl)n-pentyl, 5-phenyl-3-oxo-n-pent-1-yl and the like.

The term "$C_7$ to $C_{18}$ phenylalkylene" specifies a $C_7$ to $C_{18}$ phenylalkyl, as defined above, where the phenylalkyl radical is bonded at two different positions connecting together two separate additional groups. The definition includes groups of the formula: -phenyl-alkyl-, -alkyl-phenyl- and -alkyl-phenyl-alkyl-. Substitutions on the phenyl ring can be 1,2, 1,3 or 1,4. $C_7$ to $C_{18}$ phenylalkylenes include, for example, 1,4-tolylene and 1,3-xylylene.

Similarly, the term "$C_1$ to $C_{12}$ heterocycloalkylene" specifies a $C_1$ to $C_u$ heterocycloalkyl, as defined above, where the heterocycloalkyl radical is bonded at two different positions connecting together two separate additional groups. The definition includes groups of the formula: -heterocyclic-alkyl-, -alkyl-heterocyclic and -alkyl-heterocyclic-alkyl-.

The terms "$C_7$ to $C_{18}$ substituted phenylalkylene" and "$C_1$ to $C_{12}$ substituted heterocycloalkylene" means a $C_7$ to $C_{18}$ phenylalkylene or $C_1$ to $C_{12}$ heterocycloalkylene as defined above that is further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsul-fonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group on the phenyl ring or on the alkyl group.

The term "substituted phenyl" specifies a phenyl group substituted with one or more, and preferably one or two, moieties chosen from the groups consisting of halogen, hydroxy, protected hydroxy, cyano, nitro, $C_1$ to $C_u$ alkyl, $C_1$ to $C_{12}$ substituted alkyl, $C_1$ to $C_u$ alkoxy, $C_1$ to $C_{12}$ substituted alkoxy, $C_1$ to $C_{12}$ acyl, $C_1$ to $C_{12}$ substituted acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino, N-(phenylsulfonyl) amino or phenyl, wherein the phenyl is substituted or unsubstituted, such that, for example, a biphenyl results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(iso-propyl)phenyl, 2, 3 or 4-ethylphenyl, 2, 3 or 4-(n-propyl)phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "phenoxy" denotes a phenyl bonded to an oxygen atom, wherein the binding to the rest of the molecule is through the oxygen atom. The term "substituted phenoxy" specifies a phenoxy group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino and N-(phenylsulfonyl)amino.

The term "$C_7$ to $C_{18}$ substituted phenylalkoxy" denotes a $C_7$ to $C_{18}$ phenylalkoxy group bonded to the rest of the molecule through the oxygen atom, wherein the phenylalkyl portion is substituted with one or more, and preferably one or two, groups selected from halogen, hydroxy, protected hydroxy, oxo, protected oxo, amino, protected amino, (monosubstituted)amino, protected (monosubstituted)amino, (disubstituted)amino, guanidino, heterocyclic ring, substituted heterocyclic ring, $C_1$ to $C_{12}$ alkoxy, $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide, N,N—($C_1$ to $C_{12}$ dialkyl)carboxamide, cyano, N—($C_1$ to $C_{12}$ alkylsulfonyl)amino, thiol, $C_1$ to $C_{10}$ alkylthio, $C_1$ to $C_{10}$ alkylsulfonyl groups; and/or the phenyl group can be substituted with one or more, and preferably one or two, substituents chosen from halogen, hydroxy, protected hydroxy, cyano, nitro, $C_1$ to $C_{12}$ alkyl, $C_1$ to $C_{12}$ alkoxy, $C_1$ to $C_{12}$ acyl, $C_1$ to $C_u$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino, N-(phenylsulfonyl) amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{18}$ substituted phenylalkoxy" include groups such as 2-(4-hydroxyphenyl)ethoxy, 4-(4-methoxyphenyl)butoxy, (2R)-3-phenyl-2-amino-propoxy, (2S)-3-phenyl-2-amino-propoxy, 2-indanoxy, 6-phenyl-1-hexanoxy, cinnamyloxy, (+/−)-2-phenyl-1-propoxy, 2,2-dimethyl-3-phenyl-1-propoxy and the like.

The term "phthalimide" means a cyclic imide which is made from phthalic acid, also called 1,2-benzenedicarboxylic acid. The term "substituted phthalimide" specifies a phthalimide group substituted with one or more, and preferably one or two, moieties chosen from the groups consisting of halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino and N-(phenylsulfonyl) amino.

Examples of substituted phthalimides include 4,5-dichlorophthalimido, 3-fluorophthalimido, 4-methoxyphthalimido, 3-methylphthalimido, 4-carboxyphthalimido and the like.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_{12}$ alkyl)carboxamide, protected N—($C_1$ to $C_{12}$ alkyl)carboxamide, N,N-di($C_1$ to $C_{12}$ alkyl)carboxamide, trifluoromethyl, N—(($C_1$ to $C_{12}$ alkyl)sulfonyl)amino or N-(phenylsulfonyl)amino.

The term "naphthylene" means a naphthyl radical bonded at two positions connecting together two separate additional groups. Similarly, the term "substituted napthylene" means a naphthylene group that is further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group.

The terms "halo" and "halogen" refer to the fluoro, chloro, bromo or iodo atoms. There can be one or more halogens, which are the same or different. Preferred halogens are chloro and fluoro.

The term "(monosubstituted)amino" refers to an amino group with one substituent chosen from the group consisting of phenyl, substituted phenyl, $C_1$ to $C_{12}$ alkyl, $C_1$ to $C_{12}$ substituted alkyl, $C_1$ to $C_{12}$ acyl, $C_1$ to $C_{12}$ substituted acyl, $C_2$ to $C_{12}$ alkenyl, $C_2$ to $C_{12}$ substituted alkenyl, $C_2$ to $C_{12}$ alkynyl, $C_2$ to $C_{12}$ substituted alkynyl, $C_7$ to $C_{18}$ phenylalkyl, $C_7$ to $C_{18}$ substituted phenylalkyl, heterocyclic ring, substituted heterocyclic ring, $C_1$ to $C_{12}$ heterocycloalkyl and $C_1$ to $C_{12}$ substituted heterocycloalkyl. The (monosubstituted)amino can additionally have an amino-protecting group as encompassed by the term "protected (monosubstituted)amino."

The term "(disubstituted)amino" refers to an amino group with two substituents chosen from the group consisting of phenyl, substituted phenyl, $C_1$ to $C_u$ alkyl, $C_1$ to $C_{12}$ substituted alkyl, $C_1$ to $C_{12}$ acyl, $C_2$ to $C_{12}$ alkenyl, $C_2$ to $C_u$ alkynyl, $C_7$ to $C_{18}$ phenylalkyl, $C_7$ to $C_{18}$ substituted phenylalkyl, $C_1$ to $C_{12}$ heterocycloalkyl and $C_1$ to $C_u$ substituted heterocycloalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen. Similarly, the term "protected N—($C_1$ to $C_{12}$ alkyl)carboxamide" means there is an amino-protecting group on the carboxamide nitrogen.

The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference.

The related term "protected amino" defines an amino group substituted with an amino-protecting group discussed above.

The term "protected guanidino" as used herein refers to an "amino-protecting group" on one or two of the guanidino nitrogen atoms. Examples of "protected guanidino" groups are described by T. W. Greene and P. G. M. Wuts; M. Bodanzsky; and Stewart and Young, supra.

The term "epimino" means —NH—. The term "substituted epimino" means —N(R)—, where R is a substitution group listed above under the definition of "(monosubstituted) amino."

The term "$C_1$ to $C_5$ alkylene epimino" refers to a one to five carbon alkylene chain with an epimino at any point along the chain. The term "$C_1$ to $C_5$ substituted alkylene epimino" refers to a $C_1$ to $C_5$ alkylene epimino group that is substituted a) at the epimino position (in the same way as "substituted epimino," described above); and/or b) at one or more of the alkylene positions (in the same way as "substituted alkylene," as described above).

The term "thio" refers to —SH or, if between two other groups, —S—. The term "$C_1$ to $C_{10}$ alkylene thio" refers to a one to ten carbon alkylene chain with a thio at any point along the chain. The term "$C_1$ to $C_{10}$ substituted alkylene thio" refers to a $C_1$ to $C_{10}$ alkylene thio group that is substituted at one or more of the alkylene positions (in the same way as "substituted alkylene," as described above).

The term "sulfonyl" refers to —S(O)$_2$—. The term "$C_1$ to $C_{10}$ alkylene sulfonyl" refers to a one to ten carbon alkylene chain with a sulfonyl at any point along the chain. The term "$C_1$ to $C_{10}$ substituted alkylene sulfonyl" refers to a $C_1$ to $C_{10}$ alkylene sulfonyl group that is substituted at one or more of the alkylene positions (in the same way as "substituted alkylene," as described above).

The term "sulfinyl" refers to —S(O)—. The term "$C_1$ to $C_{10}$ alkylene sulfinyl" refers to a one to ten carbon alkylene chain with a sulfinyl at any point along the chain. The term "$C_1$ to $C_{10}$ substituted alkylene sulfinyl" refers to a $C_1$ to $C_{10}$ alkylene sulfinyl group that is substituted at one or more of the alkylene positions (in the same way as "substituted alkylene," as described above).

The term "oxy" refers to —O—. The terms "$C_1$ to $C_{10}$ alkylene oxy," "$C_1$ to $C_{10}$ alkylene dioxy" and "$C_1$ to $C_{10}$ alkylene trioxy" refer to a one to ten carbon alkylene chain with, respectively, one, two or three —O— at any point along the chain, provided that no two oxygen atoms are consecutive, and provided that any two oxygen atoms are separated by at least two carbons. The terms "$C_1$ to $C_{10}$ substituted alkylene oxy," "$C_1$ to $C_{10}$ substituted alkylene dioxy" and "$C_1$ to $C_{10}$ substituted alkylene trioxy" refer, respectfully to "$C_1$ to $C_{10}$ alkylene oxy," "$C_1$ to $C_{10}$ alkylene dioxy" and "$C_1$ to $C_{10}$ alkylene trioxy" that are substituted at one or more of the alkylene positions (in the same way as "substituted alkylene," as described above).

The term "thiocarbonyl" refers to —C(S)H or, if between two other groups, —C(S)—. The term "thioester" refers to —C(O)SH or, if between two other groups, —C(O)S—.

The term "carboxy-protecting group" as used herein refers to one of the ester derivatives of the carboxylic acid group commonly employed to block or protect the carboxylic acid group while reactions are carried out on other functional groups on the compound. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl) dimethylsilyl, 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydroxymethyl" which refer to a hydroxy or hydroxymethyl substituted with one of the above hydroxy-protecting groups.

The term "$C_1$ to $C_{10}$ alkylthio" refers to sulfide groups such as methylthio, ethylthio, n-propylthio, isopropylthio, n-butylthio, t-butylthio and like groups.

The term "$C_1$ to $C_{10}$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like. The term "$C_1$ to $C_{10}$ alkylsulfonyl" encompasses groups such as methylsulfonyl, ethylsulfonyl, n-propylsulfonyl, isopropylsulfonyl, n-butylsulfonyl, t-butylsulfonyl and the like. it should also be understood that the above thio, sulfoxide or sulfonyl groups can be at any point on the alkyl chain (e.g., 2-methylmercaptoethyl).

The terms "$C_1$ to $C_{10}$ substituted alkylthio," "$C_1$ to $C_{10}$ substituted alkylsulfoxide," and "$C_1$ to $C_{10}$ substituted alkylsulfonyl," denote the $C_1$ to $C_{10}$ alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "$C_1$ to $C_{12}$ alkylaminocarbonyl" means a $C_1$ to $C_{12}$ alkyl attached to a nitrogen of the aminocarbonyl group. Examples of $C_1$ to $C_{12}$ alkylaminocarbonyl include methylaminocarbonyl, ethylaminocarbonyl, propylaminocarbonyl and butylaminocarbonyl. The term "$C_1$ to $C_{12}$ substituted alkylaminocarbonyl" denotes a substituted alkyl bonded to a nitrogen of the aminocarbonyl group, which alkyl may be substituted as described above in relation to $C_1$ to $C_{12}$ substituted alkyl. Examples of $C_1$ to $C_{12}$ substituted alkylaminocarbonyl include, for example, methoxymethylaminocarbonyl, 2-chloroethylaminocarbonyl, 2-oxopropylaminocarbonyl and 4-phenylbutylaminocarbonyl.

The term "$C_1$ to $C_{12}$ alkoxycarbonyl" means a "$C_1$ to $C_{12}$ alkoxy" group attached to a carbonyl group. The term "$C_1$ to $C_{12}$ substituted alkoxycarbonyl" denotes a substituted alkoxy bonded to the carbonyl group, which alkoxy may be substituted as described above in relation to "$C_1$ to $C_{12}$ substituted alkyl."

The term "phenylaminocarbonyl" means a phenyl attached to a nitrogen of the aminocarbonyl group. The term "substituted phenylaminocarbonyl" denotes a substituted phenyl bonded to a nitrogen of the aminocarbonyl group, which phenyl may be substituted as described above in relation to substituted phenyl. Examples of substituted phenylaminocarbonyl include 2-chlorophenylaminocarbonyl, 3-chlorophenylaminocarbonyl, 2-nitorphenylaminocarbonyl, 4-biphenylaminocarbonyl, and 4-methoxyphenylaminocarbonyl.

The term "$C_1$ to $C_{12}$ alkylaminothiocarbonyl" means a $C_1$ to $C_{12}$ alkyl attached to an aminothiocarbonyl group, wherein the alkyl has the same meaning as defined above. Examples of $C_1$ to $C_{12}$ alkylaminothiocarbonyl include methylaminothiocarbonyl, ethylaminothiocarbonyl, propylaminothiocarbonyl and butylaminothiocarbonyl.

The term "$C_1$ to $C_{12}$ substituted alkylaminothiocarbonyl" denotes a substituted alkyl bonded to an aminothiocarbonyl group, wherein the alkyl may be substituted as described above in relation to $C_1$ to $C_{12}$ substituted alkyl. Examples of $C_1$ to $C_{12}$ substituted alkylaminothiocarbonyl include, for example, methoxymethylaminothiocarbonyl, 2-chloroethylaminothiocarbonyl, 2-oxopropylaminothiocarbonyl and 4-phenylbutylaminothiocarbonyl.

The term "phenylaminothiocarbonyl" means a phenyl attached to an aminothiocarbonyl group, wherein the phenyl has the same meaning as defined above. The term "substituted phenylaminothiocarbonyl" denotes a substituted phenyl bonded to an aminothiocarbonyl group, wherein phenyl may be substituted as described above in relation to substituted phenyl. Examples of substituted phenylaminothiocarbonyls include 2-chlorophenylaminothiocarbonyl, 3-chlorophenylaminothiocarbonyl, 2-nitorphenylaminothiocarbonyl, 4-biphenylaminothiocarbonyl and 4-methoxyphenylaminothiocarbonyl.

The term "phenylene" means a phenyl group where the phenyl radical is bonded at two positions connecting together two separate additional groups. Examples of "phenylene" include 1,2-phenylene, 1,3-phenylene, and 1,4-phenylene.

The term "substituted phenylene" means a phenyl group where the phenyl radical is bonded at two positions connecting together two separate additional groups, wherein the phenyl is substituted as described above in relation to "substituted phenyl."

The term "substituted $C_1$ to $C_{12}$ alkylene" means a $C_1$ to $C_{12}$ alkyl group where the alkyl radical is bonded at two positions connecting together two separate additional groups and further bearing an additional substituent. Examples of "substituted $C_1$ to $C_{12}$ alkylene" includes aminomethylene, 1-(amino)-1,2-ethyl, 2-(amino)-1,2-ethyl, 1-(acetamido)-1,2-ethyl, 2-(acetamido)-1,2-ethyl, 2-hydroxy-1,1-ethyl, 1-(amino)-1,3-propyl.

The terms "cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the cyclic $C_2$ to $C_7$ heteroalkylene.

The cyclic alkylene or heteroalkylene group may be substituted once or twice by the same or different substituents which, if appropriate, can be connected to another part of the compound (e.g., alkylene) selected from the group consisting of the following moieties: hydroxy, protected hydroxy, carboxy, protected carboxy, oxo, protected oxo, $C_1$ to $C_4$ acyloxy, formyl, $C_1$ to $C_{12}$ acyl, $C_1$ to $C_{12}$ alkyl, $C_1$ to $C_7$ alkoxy, $C_1$ to $C_{10}$ alkylthio, $C_1$ to $C_{10}$ alkylsulfoxide, $C_1$ to $C_{10}$ alkylsulfonyl, halo, amino, protected amino, (monosubstituted) amino, protected (monosubstituted)amino, (disubstituted) amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the benzene radical is fused to a pyridino, pyrano, pyrrolo, pyridinyl, dihydropyrrolo, or dihydropyridinyl ring. Examples of fused cyclic groups which each contain one oxygen atom and one or two double bonds are when the benzene radical ring is fused to a furo, pyrano, dihydrofurano, or dihydropyrano ring. Examples of fused cyclic groups which each have one sulfur atom and contain one or two double bonds are when the benzene radical is fused to a thieno, thiopyrano, dihydrothieno or dihydrothiopyrano ring. Examples of cyclic groups which contain two heteroatoms selected from sulfur and nitrogen and one or two double bonds are when the benzene radical ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "carbamoyl" means an —NC(O)— group where the radical is bonded at two positions connecting two separate additional groups.

One or more of the compounds of the invention, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1-19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when a position is substituted with a (quaternary ammonium) methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

It should be understood that any position of the claimed invention has up to three serial "substitutions." For example, a "substituted alkyl" that is substituted with a "substituted phenyl" that is, in turn, substituted with a "substituted alkyl" can, in turn, be susbstitued by one more group and no longer further substituted. However, it should also be understood that the invention contemplates, if appropriate, more than three parallel susbstitutions. For example, if appropriate, more than three hydrogens on an alkyl moiety may be substituted with any one or more of a variety of groups, including halo and hydroxy.

Synthesis of IA derivatives has been described in Cholody W M et al., J. Med. Chem. (1990) 33, 49-52; Cholody W M et al., J. Med. Chem. (1992) 35, 378-382; and Cholody W M et al., J. Med. Chem. (1996) 39, 1028-1032; U.S. Pat. No. 5,231,100; and U.S. Pat. No. 6,229,015. See also Capps et al., EP application 145226 (1985); Tarasov et al., Photochem. Photobiol. 70:568-578 (1999); Cholody et al., J. Med. Chem. 38:3043-3052 (1995); Idem., EP Application 0502668 (1992); U.S. Pat. No. 5,508,289; and PCT application WO97/38999 (1997.

Specific examples of IA derivatives synthesis are as follows:

A. 1-[[2-(Diethylamino)ethyl]amino]-7-methoxy-4-nitro-9(10H)-cridinone

A mixture of 4.57 g (0.015 mol) 1-chloro-7-methoxy-4-nitro-9(10H)-acridinone, 25 ml DMF and 7.00 g (0.06 mol) 2-diethylaminoethylamine is stirred and heated at 60.degree. C. for 30 minutes. 100 ml 40% (v/v) MeOH-water solution is added to the reaction mixture, heated to boiling and after cooling left overnight in a refrigerator. The crystallized product is collected by filtration washed with water (150 ml) and MeOH (50 ml) and dried to give 5.30 g. (92%) analytically pure product as yellow needles: mp 178.degree.-179.degree. C. (lit. mp. Capps. D. B. European Patent Appl. E.P. 145226, 1985; Chem. Abstr. 1985, 103, 215182s. 179.degree.-180.degree. C.);

B. 7-Substituted 4-amino-1-[[(dialkylamino)alkyl]amino]-4-nitro-9(10H)-acridinone hydrochloride salts To a mixture of nitro derivatives (0.01 mol), 200 ml THF, and about 2.5 g of Raney Ni is added with stirring at room temperature then 2 ml hydrazine monohydrate, and stirring if continued for about 30 minutes. The catalyst is filtered off and washed with THF (50 ml). The filtrate is quickly treated with 10 ml concentrated hydrochloric acid and stirred for 10 minutes. The yellow precipitate obtained is collected and washed with THF. The product is recrystallized from a solution of MeOH (90%)-dioxane made acidic with HCl (pH.about.2).

C. 5-[[2-(Diethylamino)ethyl]amino]-8-methoxyimidazo[4,5,1-de]acridin-6-one Dihydrochloride A mixture of 1.71 g (4 mmol) of the product from the procedure of Example 1B and 20 ml (95% formic acid is heated at reflux for 6 h. Acid is evaporated and the residue is dissolved in water (100 ml). The solution is made basic (pH 9) by addition of sodium carbonate and product is extracted with chloroform (2.times.100 ml). The organic extracts are dried and evaporated to give a residue which is dissolved in EtOH. The solution is made acidic with HCl and product is crystallized by addition of acetone to give the title product.

As discussed above, the present invention contemplates methods of testing IA derivative compounds against certain conditions including cancer and autoimmune condtions, as well as improving the satus of a subject with such a condition.

Thus, the present invention relates to screening methods for identifying compounds that kill or inhibit the growth of cancer cells, but, at least to a lesser extent, not their non-cancer cell counterparts. In one embodiment, the invention relates to a method of identifying an IA compound that selectively kills or inhibits the growth of (is toxic to) engineered human tumorigenic cells, comprising contacting test cells, which are engineered human tumorigenic cells, with a candidate agent; determining viability of test cells contacted with the candidate agent; and comparing the viability of the test cells with the viability of an appropriate control. In all embodiments, viability is assessed by determining the ability of the IA compound to kill cells or inhibit growth/proliferation of cells, or both. If the viability of the test cells is less than that of the control cells, then the IA compound that is selectively toxic to kill or inhibit the growth of engineered human tumorigenic cells is identified. An appropriate control is a cell that is the same type of cell as the test cell, except that the control cell is not engineered to be tumorigenic. For example, control cells may be the parental primary cells from which the test cells are derived. Control cells are contacted with the candidate IA compound under the same conditions as the test cells. An appropriate control may be run simultaneously, or it may be pre-established (e.g., a pre-established standard or reference).

In one embodiment, the method of identifying an agent selectively toxic to tumorigenic cells comprises further assessing the toxicity of an IA compound identified as a result of screening in engineered human tumorigenic cells in an appropriate animal model or in an additional cell-based or non-cell-based system or assay. For example, an IA compound so identified can be assessed for its toxicity to cancer cells such as tumor cells or leukemia cells obtained from individuals or its toxicity to a (one or more) cancer (tumor) cell line. For example, the method can comprise further assessing the selective toxicity of an IA compound to tumorigenic cells in an appropriate mouse model or nonhuman primate.

The invention additionally relates to a method of identifying compounds of the invention that are toxic to engineered tumorigenic cells, such as engineered human tumorigenic cells. In one embodiment, the invention relates to a method of identifying a compound that kills or inhibits the growth of (is toxic to) engineered human tumorigenic cells, comprising contacting test cells, which are engineered human tumorigenic cells, with the compound; determining viability of the test cells contacted with the compound; and comparing the viability of the test cells with the viability of an appropriate control. If the viability of the test cells is less than that of the control cells, then a compound that is toxic to (kills or inhibits the growth of) engineered human tumorigenic cells is identified. An appropriate control is a cell that is the same type of cell (e.g. engineered human tumorigenic cell) as the test cells, except that the control cell is not contacted with the candidate agent. An appropriate control may be run simultaneously, or it may be pre-established (e.g., a pre-established standard or reference). For example, a compound so identified can be assessed for its toxicity to cancer cells obtained from individuals or its toxicity to a (one or more) cancer (tumor) cell line.

Regarding testing compounds of the invention for improving the condition of a subject with an autoimmune disease, one suitable cell based assay is the mixed lymphocyte reaction (MLR). Current Protocols in Immunology, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assessed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. Current Protocols in Immunology, above, 3.15, 6.3.

A proliferative T cell response in an MLR assay may be due to direct mitogenic properties of an assayed molecule or to external antigen induced activation. Additional verification of the T cell stimulatory activity of the compound can be obtained by a co-stimulation assay. T cell activation requires an antigen specific signal mediated through the T-cell receptor (TCR) and a costimulatory signal mediated through a second ligand binding interaction, for example, the B7 (CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive co-stimulation effect of T cell activation; conversely, CTLA-4 binding to B7 has a T cell deactivating effect. Chambers, C. A. and Allison, J. P., Curr. Opin. Immunol. (1997) 9:396. Schwartz, R. H., Cell (1992) 71:1065; Linsey, P. S, and Ledbetter, J. A., Annu. Rev. Immunol. (1993) 11:191; June, C. H. et al, Immunol. Today (1994) 15:321; Jenkins, M. K., Immunity (1994) 1:405. In a costimulation assay, a compound is assayed for T cell costimulatory or inhibitory activity.

The results of the cell based in vitro assays can be further verified using in vivo animal models and assays for T-cell function. A variety of well known animal models can be used to test the efficacy of a molecule. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., Fundamental Immunology, 2nd ed., W. E. Paul ed., Raven Press, NY, 1989, 889-992. A suitable procedure is described in detail in Current Protocols in Immunology, above, unit 4.4. Other transplant rejection models which can be used to test the compounds of the invention are the allogeneic heart transplant models described by Tanabe, M. et al, Transplantation (1994) 58:23 and Tinubu, S. A. et al, J. Immunol. (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in Current Protocols in Immunology, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., Multiple Sclerosis (1995) 1:143. Both acute and relapsing-remitting models have been developed. The compounds of the invention can be tested for T cell stimulatory or inhibitory activity against immune mediated demyelinating disease using the protocol described in Current Protocols in Immunology, above, units 15.1 and 15.2. See also the models for myelin disease in which oligodendrocytes or Schwann cells are grafted into the central nervous system as described in Duncan, I. D. et al, Molec. Med. Today (1997) 554-561.

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in Current Protocols in Immunology, Eds. J. E. Cologan, A. M. Kruisbeek, D. H. Margulies, E. M. Shevach and W. Strober, John Wiley & Sons, Inc., 1994, unit 4.2. See also Grabbe, S, and Schwarz, T, Immun. Today 19 (1): 37-44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., Immunology (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al, Am. J. Respir. Cell Mol. Biol. (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al, Nat. Med. (1997) 3:183, in which the mice demonstrate histopathologic skin lesions resembling psoriasis. Another suitable model is the human skin/scid mouse chimera prepared as described by Nickoloff, B. J. et al, Am. J. Path. (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., Proc. Nail. Acad. Sci. USA 82, 6148-615 [1985]); gene targeting in embryonic stem cells (Thompson et al., Cell 56, 313-321 [1989]); electroporation bf embryos (Lo, Mol. Cel. Biol. 3, 1803-1814 [1983]); sperm-mediated gene transfer (Lavitrano et al., Cell 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89, 6232-636 (1992). The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, an agent that blocks a test compound is administered to the animal and the effect on immune function is determined.

Examples of types of cancers contemplated by the present invention include benign tumors, neoplasms or tumors (such as carcinomas, sarcomas, adenomas or myeloid lymphoma tumors, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon sarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hematoma, bile duct carcinoma, melanoma, choriocarcinoma, semicoma, embryonal carcinoma, Wilms' tumor, cervical cancer, testicular tumor, lung carcinoma, small cell carcinoma, bladder carcinoma, epithelial carcinoma, glioma, astrocytoma, medulloblastoma, craniopharyngioma, ependynoma, pinealoma, hemangioblastoma, retinoblastoma), leukemias, (e.g. acute lymphocytic leukemia), acute myelocytic leukemia (myelolastic, promyelocytic, myelomonocytic, monocytic and erythroleukemia), chronic leukemias (chronic myelocytic (granulocytic) leukemia and chronic lymphocytic leukemia), or polycythemia vera, or lymphomas (Hodgkin's disease and non-Hodgkin's diseases), multiple myelomas and Waldenstrom's macroglobulinemia.

Autoimmune disorders, diseases, or conditions for which the compounds and methods of the invention apply include, but are not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), multiple sclerosis, neuritis, uveitis ophthalmia, polyendocrinopathies, purpura (e.g., Henloch-Scoenlein purpura), Reiter's Disease, Stiff-Man Syndrome, autoimmune pulmonary inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis), systemic lupus erhythematosus, discoid lupus, Goodpasture's syndrome, Pemphigus, receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen BLyS binding polypeptides, mixed connective tissue disease, polymyositis/dermatomyositis, pernicious anemia, idiopathic Addison's disease, infertility, glomerular nephritis such as primary glomerular nephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

The compositions of the invention are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. As used herein, an "effective amount" of the siRNA is preferably an amount sufficient to cause RNAi-mediated degradation of the target mRNA in a subject.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

One skilled in the art can readily determine an effective amount of a compound of the invention to be administered to a given subject, by taking into account factors such as the size and weight of the subject; the extent of disease penetration; the age, health and sex of the subject; the route of administration; and whether the administration is regional or systemic.

A compound of the invention can be administered to a subject in combination with another therapeutic method designed to treat the pathology. For example, a compound of the invention can be administered in combination with therapeutic methods currently employed for treating cancer or preventing metastasis (e.g., radiation therapy, other chemotherapy, and surgery). Examples of other chemotherapeutic agents include cisplatin, carboplatin, cyclophosphamide, 5-fluorouracil, adriamycin, daunorubicin ortamoxifen.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal. The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention will now be described further by way of illustration only by reference to the following non-limiting Examples. Further embodiments of the invention will occur to those skilled in the art in the light of these.

Materials and Methods

Drugs and Chemicals: MTT [3-(4,5-dimethylthiazol-2-yl)-2,5-diphenyltetrazolium bromide] and tetramethylrosamine were obtained from Sigma Chemical Co. (St. Louis, Mo.). Fumitremorgin C (FTC) was, kindly provided by Dr. S. E. Bates, National Cancer Institute, Bethesda, Md. G-418 hydrochloride was purchased from Calbiochem-Novabiochem, San Diego, Calif.

Tissue culture: Human non-small cell lung cancer A549 cells and T-cell leukemia CCRF-CEM cells were grown under monolayer conditions or up to a maximal density of 106 cells/ml (for CCRF-CEM cells) in RPMI-1640 medium (GIBCO) supplemented with 10% fetal calf serum, 2 mM glutamine, 100 µg/ml penicillin and 100 µg/ml streptomycin (Biological Industries, Beth-Haemek, Israel) in a humid atmosphere of 5% $CO_2$. Drug resistant A549/K1.5 cells with ABCG2 overexpression were maintained under a continuous drug selection with 1.5 µM C-1305. Bram, E. E., et al., (2007) *Biochem Pharmacol* 74(1), 41-53.

For cytotoxicity and accumulation experiments, cells were grown in drug-free medium for at least one week prior to the experiments. Human embryonic kidney cells (HEK293) and their stable transfectants overexpressing the R482, G482 and T482 ABCG2 were grown in the above RPMI-1640 medium supplemented with 2 mg/ml G-418. Bram, E. E., et al., (2006) *Cancer Chemother Pharmacol* 58(6), 826-834.

Cytotoxicity and growth inhibition assays: The cytotoxic activity of the various IA antitumor agents was determined using the MTT assay. Poindessous, V., et al., (2003) *Clin Cancer Res* 9(7), 2817-2825.

EXAMPLE 1

This example shows the resistance levels of various IA derivative compounds.

Exponentially growing cells were seeded at 5×103 cells/well in 24-well plates (2 ml medium/well). Following an overnight incubation, cells were exposed to different drug concentrations for 96 hours. Cellular viability was determined by adding the tetrazolium salt MTT for 4 h at 37° C., followed by solubilization of the intracellular precipitated formazan in 1 ml DMSO and absorbance was determined by a microplate reader (ASYS Hitech GmbH, Austria). Drug concentrations required to inhibit cell growth by 50% (IC50) compared with untreated controls were determined from the curves of survival versus drug concentrations using the Slide-Write software (Advanced Graphics Software, Inc., Encinitas, Calif.). Resistance folds (RF) were calculated by dividing the IC50 value of the resistant cells by that of the parental cell line. Values presented are means of at least three independent experiments, each performed in duplicates.

To assess the levels of drug resistance of A549/K1.5 cells to a series of 23 IA analogues differing only at 7 defined residues revolving their common core structure, as shown in Table I:

TABLE I

R6, O, NH(CH$_3$)$_n$NR$_{a,b}$, R1, R2, R3, R14, xHCl, N, N

|  |  | R1 | R2 | R3 | R6 | R14 | R$_{a,b}$ | n |
|---|---|---|---|---|---|---|---|---|
| Group A | C-1584 | OH | H | H | H | H | Me | 2 |
|  | C-1311 | OH | H | H | H | H | Et | 2 |
|  | C-1371 | OH | H | H | H | H | Me | 3 |
|  | C-1335 | OH | H | H | H | H | Et | 3 |
|  | C-1309 | OH | H | H | H | Me | Me | 2 |
|  | C-1310 | OH | H | H | H | Me | Et | 2 |
|  | C-1338 | OH | H | H | H | Me | Et | 3 |
|  | C-1492 | OH | H | H | H | H | Me | 5 |
|  | C-1419 | H | OH | H | H | H | Et | 2 |
|  | C-1633 | H | H | OH | H | H | Et | 2 |
| Group B | C-1176 | H | H | H | H | H | Me | 2 |
|  | C-1415 | H | H | H | H | H | Et | 2 |
|  | C-1212 | H | H | H | H | H | Me | 3 |
|  | C-1213 | H | H | H | H | Me | Me | 2 |
|  | C-1266 | H | H | H | H | H | Me | 5 |
|  | C-1503 | H | H | OMe | OMe | H | Et | 2 |
|  | C-1554 | Me | H | H | H | H | Et | 2 |
|  | C-1330 | OMe | H | H | H | H | Et | 2 |
|  | C-1558 | t-butyl | H | H | H | H | Et | 2 |
|  | C-1375 | OMe | H | H | H | Me | Me | 3 |
|  | C-1379 | OMe | H | H | H | Me | Et | 3 |
|  | C-1315 | OH | H | H | H | Me | Bu | 2 |
|  | C-2018 | OH | H | H | H | H | Et | 9 |

MTT-based cytotoxicity assays were used, as shown in Table II:

TABLE II

|  | Drug | IC50 (µM) A549 | IC50 (µM) A549/K1.5 | RF |
|---|---|---|---|---|
| Group A | C-1309 | 0.05 ± 0.007 | 3.22 ± 0.180 | 60.80 |
|  | C-1336 | 0.058 ± 0.12 | 2.41.1 ± 1.1 | 41.55 |
|  | C-1310 | 0.06 ± 0.008 | 1.22 ± 0.070 | 20.30 |
|  | C-1584 | 0.01 ± 0.002 | 0.25 ± 0.010 | 19.20 |
|  | C-1371 | 0.04 ± 0.006 | 0.70 ± 0.030 | 17.90 |
|  | C-1335 | 0.09 ± 0.004 | 1.00 ± 0.250 | 11.10 |
|  | C-1419 | 2.92 ± 0.420 | 31.26 ± 2.550 | 10.70 |
|  | C-1492 | 1.69 ± 0.120 | 17.17 ± 1.950 | 10.10 |
|  | C-1311 | 0.27 ± 0.012 | 2.34 ± 0.050 | 8.70 |
|  | C-1633 | 2.26 ± 0.330 | 9.83 ± 1.440 | 4.35 |
| Group B | C-1315 | 1.69 ± 0.260 | 3.46 ± 0.160 | 2.05 |
|  | C-1558 | 1.48 ± 0.250 | 2.51 ± 0.170 | 1.70 |
|  | C-1554 | 2.02 ± 0.330 | 3.07 ± 0.800 | 1.51 |
|  | C-1213 | 12.28 ± 2.500 | 18.27 ± 2.400 | 1.49 |
|  | C-2018 | 1.54 ± 0.310 | 2.13 ± 0.620 | 1.38 |
|  | C-1212 | 1.89 ± 0.420 | 1.93 ± 0.840 | 1.02 |
|  | C-1375 | 1.30 ± 0.060 | 1.25 ± 0.110 | 0.96 |
|  | C-1415 | 2.70 ± 0.210 | 2.38 ± 0.120 | 0.88 |
|  | C-1503 | 3.50 ± 0.640 | 3.09 ± 0.740 | 0.88 |
|  | C-1379 | 1.07 ± 0.030 | 0.68 ± 0.060 | 0.63 |
|  | C-1176 | 2.35 ± 0.750 | 1.21 ± 0.650 | 0.51 |
|  | C-1330 | 2.16 ± 0.270 | 0.97 ± 0.080 | 0.45 |
|  | C-1266 | 2.81 ± 0.270 | 0.56 ± 0.002 | 0.20 |

Figure 2:
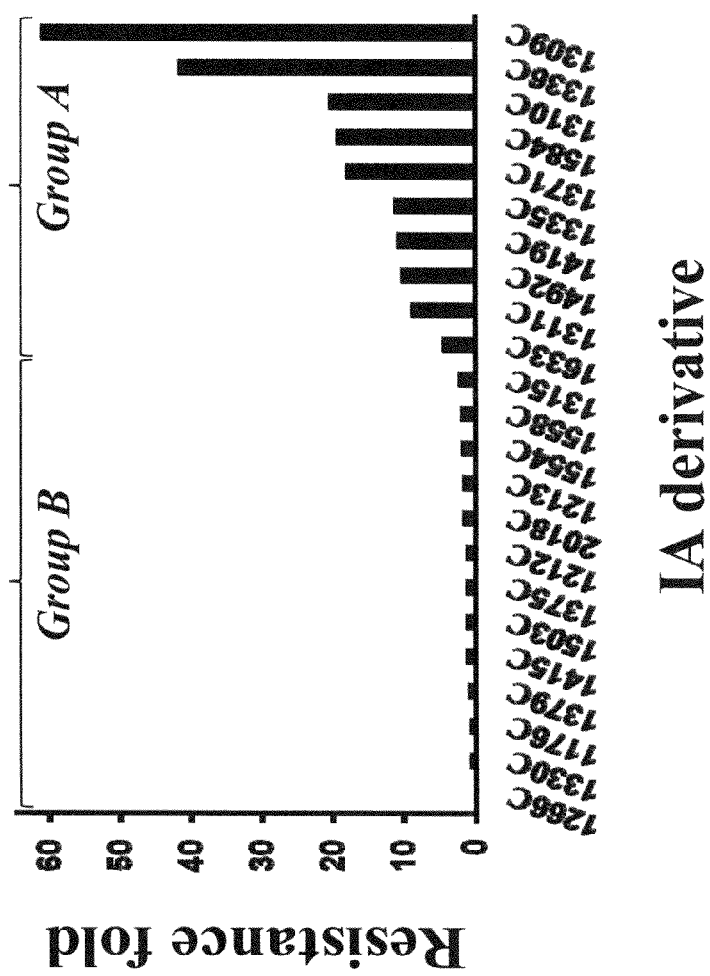
FIG. 2 shows the resistance fold of ABCG2 expressing human non-small cell lung cancer A549/K1.5 cells to 23 IA derivatives described below, when compared to parental A549 cells. Parental A549 cells and ABCG2 overexpressing A549/K1.5 cells were exposed for 96 hours to increasing concentrations of the various 23 IA derivatives followed by IC50 analysis using a colorimetric—MTT assay. The results depicted represent resistance fold (RF) of ABCG2 expressing A549/K1.5 cells over IC50 values of parental A549 cells.

The above results show that A549/K1.5 cells displayed a differential resistance towards certain IA derivatives, consequently subdividing them into two distinct groups (P-value=0.0007) A and B, representing drugs to which ABCG2 overexpression confers resistance or fails to do so, respectively (see Table I and FIG. 2). Specifically, A549/K1.5 cells exhibited a prominent resistance to C-1311 as well as to 9 other IA derivative compounds including C-1309, C-1336, C-1310, C-1584, C1371, C-1335, C-1419, C-1492 and C-1633 (group A), with up to 61-fold resistance to C-1309. In contrast, A549/K1.5 cells essentially retained parental cell sensitivity to the 13 remaining IAs (group B), with the exception of C-1330 and C-1266 to which A549/K1.5 cells displayed 2.2- and 5.0-fold hypersensitivity, respectively (Table II and FIG. 2).

These results establish that ABCG2 recognizes certain IA derivatives but fails to do so with other IA derivatives. Drug resistance correlates with reduced cellular accumulation of IA derivatives: The results above suggested that overexpression of ABCG2 is the molecular mechanism underlying resistance of A549/K1.5 cells to group A IAs.

EXAMPLE 2

Assaying IA derivative cellular accumulation

In order to corroborate this finding, the ability of ABCG2 to extrude IA derivatives from A549/K1.5 cells was explored using the intrinsic fluorescent properties of IAs in a flow cytometric assay.

In this assay, one ml aliquots of A549/K1.5 or CCRF-CEM cell suspensions (1×106 cells/ml) in growth medium containing 20 mM Hepes at pH 7.3 were distributed into 1.5 ml polypropylene Eppendorf test tubes. Then, IA derivative compounds were added at various concentrations of 0.01 to 200 µM, in the presence or absence of the specific ABCG2 efflux inhibitor FTC (5 µM) and allowed to incubate for 1 h at 37° C. Rabindran, S. K., et al., (2000) *Cancer Res* 60(1), 47-50.

Alternatively, in time-course experiments, IA derivatives at a constant concentration of 10 µM were added to a CCRF-CEM cell suspension incubated at 37° C., and 1 ml aliquots were removed at variable time points up to 1 hour. Following incubation, test tubes were transferred to ice and centrifuged at 4° C. Cells were then washed twice and re-suspended in ice-cold PBS containing 1% fetal calf serum and kept in the dark at 4° C. until analysis.

IA derivative and tetramethylrosamine (TMR) accumulation in parental HEK293 and their HEK293/ABCG2 R/G/T482 transfectants were carried out as described herein with the a slight amendment of using a single IA concentration of 1 µM ±FTC (5 µM) for the selected as well as 0.1 µM for TMR accumulation. Robey, R. W., et al., (2003) *Br J Cancer* 89(10), 1971-1978. Cellular fluorescence was determined using a FACSCalibur (BD Bioscience, San Jose, Calif. USA) flow cytometer. FL1-H excitation of IAs was at 488 nm and emission was collected at 525 nm, whereas FL2-H excitation of TMR was at 550 nm and emission was collected at 574 nm. Flow cytometric results are presented as means±SD of 3 independent experiments.

In immunofluorescence microscopy of plasma membrane targeting of ABCG2 and nuclear accumulation of IAs, cells (1×104/well) were seeded in 24-well plates (1 ml medium/well) and incubated for 2 days, following which some wells were supplemented with 10 µM IA-containing medium±5 µM FTC and incubated for 1 h at 37° C. Cells were then washed twice with ice-cold PBS containing 0.1% BSA and blocked for 10 min at 4° C. with PBS containing 5% BSA. Cells were then washed once with ice-cold PBS containing 0.1% BSA and incubated for 30 min at 4° C. with a Phycoerythrin-conjugated, affinity-purified 5D3 mouse anti-human ABCG2 monoclonal antibody (1:100; eBioscience). Unspecific fluorescence was determined using cells that were incubated only with a secondary Phycoerythrin (PE)-conjugated goat anti-mouse IgG (1:200; Jackson Immunoresearch Labs, West Grove, Pa.). Cells were then washed twice and subjected to fluorescence microscopy using a DMIRE2 fluorescence microscope equipped with a DC300FX camera (Leica Microsystems, Wetzlar, Germany).

Quantitative evaluation of ABCG2 interaction with various IA derivatives: The extent of ABCG2-mediated resistance was expressed using the Resistance Fold (RF) parameter representing the ratio between the IC50 values of the resistant cells and parental cells. Likewise, ABCG2-dependent differential accumulation of IAs in ABCG2-overexpressing A549/K1.5 cells was compared using the ratio of IA accumulation in the presence or absence of the potent ABCG2 inhibitor FTC. This was termed the FTC-dependent Accumulation Fold (AF) and was determined for each IA at a constant IA concentration of 10 µM. Accumulation of IAs at a constant 10 µM concentration was found to be both readily detectable by flow cytometry yet at non-saturating levels and within the linear dose-dependent range of drug accumulation.

A549/K1.5 cells displayed a complete exclusion of group A IA derivatives, up to high micromolar drug concentrations (see representative IA derivative of both groups A and B, FIGS. 3A and 3B). Furthermore, addition of the specific ABCG2 transport inhibitor FTC resulted in a dose-dependent restoration of accumulation of group A IAs (FIG. 3A). In contrast, A549/K1.5 cells accumulated group B IA derivatives in a dose-dependent manner regardless of the presence or absence of FTC (FIG. 3B).

To quantify the ABCG2-dependent component of IA accumulation in A549/K1.5 cells, a parameter of FTC-inducible accumulation fold (AF; see Materials and Methods) was used for each IA derivative at a constant IA concentration of 10 µM. Quantitative analysis revealed the same IA cluster distribution observed in the above cytotoxicity assay (P-value=0.0002; compare FIG. 3C with FIG. 2). Thus, group A IA derivatives exhibited high AF values ranging from 9.4 to 47.1, representing the FTC-reversible, ABCG2-dependent restoration of IA drug accumulation. In contrast, group B IA derivatives consisting of non-ABCG2 substrates retained AF values close to 1.0. Moreover, when plotting the RF values against the AF values, a distinct separation was observed between these clusters, with an integrated average cluster difference of 16.8-fold (FIG. 3D). Accordingly, this 2-dimensional functional representation defines and subdivides these IA compounds into two distinct groups regarding ABCG2-mediated drug efflux and consequent drug resistance.

Nuclear localization is a hallmark of intracellular accumulation of IA derivative compounds. Thus, C-1311 and other acridine-based compounds display nuclear accumulation and exert their cytotoxic activity via direct interactions with DNA as well as with DNA modifying enzymes including topoisomerase I or II. Robey, R. W., et al., (2003) *Br J Cancer* 89(10), 1971-1978; Topcu, Z. (2001) gJ Clin Pharm Ther 26(6), 405-416.

In order to exclude the possibility that differential subcellular accumulation of IA derivatives is the basis of the observed difference in cytotoxicity and cellular fluorescence, A549/K1.5 cells were incubated with 10 µM of selected IA derivatives from both group A and B in the presence or absence of FTC and subjected to fluorescence microscopy. Consistent with the flow cytometric results (FIGS. 3A-C), group A compounds C-1311 and C-1310 showed no apparent intracellular accumulation in A549/K1.5 cells which functionally overexpress ABCG2 at the plasma membrane (red fluorescence, FIGS. 4A and 4C). However, a marked restoration of nuclear accumulation of these ABCG2 substrates occurred upon inhibition of ABCG2 transport function by FTC (green fluorescence, FIGS. 4B and 4D). In contrast, the non-ABCG2 substrate C-1266 from group B displayed comparable and significant nuclear accumulation regardless of ABCG2 inhibition by FTC (FIGS. 4E and 4F).

In addition, group A and B IA derivatives accumulate in a comparable dose- and time-dependent manner in ABCG2-null CCRF-CEM leukemia cells. Intracellular drug accumulation is thought to represent a net drug influx superceding all cellular efflux mechanisms including those mediated by ABC transporters. Therefore, in order to rule out the possibility that the observed difference in intracellular accumulation of IA derivatives and subsequent cytotoxicity represented differential IA influx kinetics, the cellular influx rates of representative group A and B IA derivatives in ABCG2-null CCRF-CEM human leukemia cells were compared. Turner, J. G., et al., (2006) *Blood* 108(12), 3881-3889. Comparable influx rates were observed for representative IA derivatives from both groups A and B, supporting the conclusion that an ABCG2-dependent, differential IA efflux capacity is the mechanism underlying decreased intracellular accumulation of group A IA derivatives (FIG. 5A).

Figure 5:
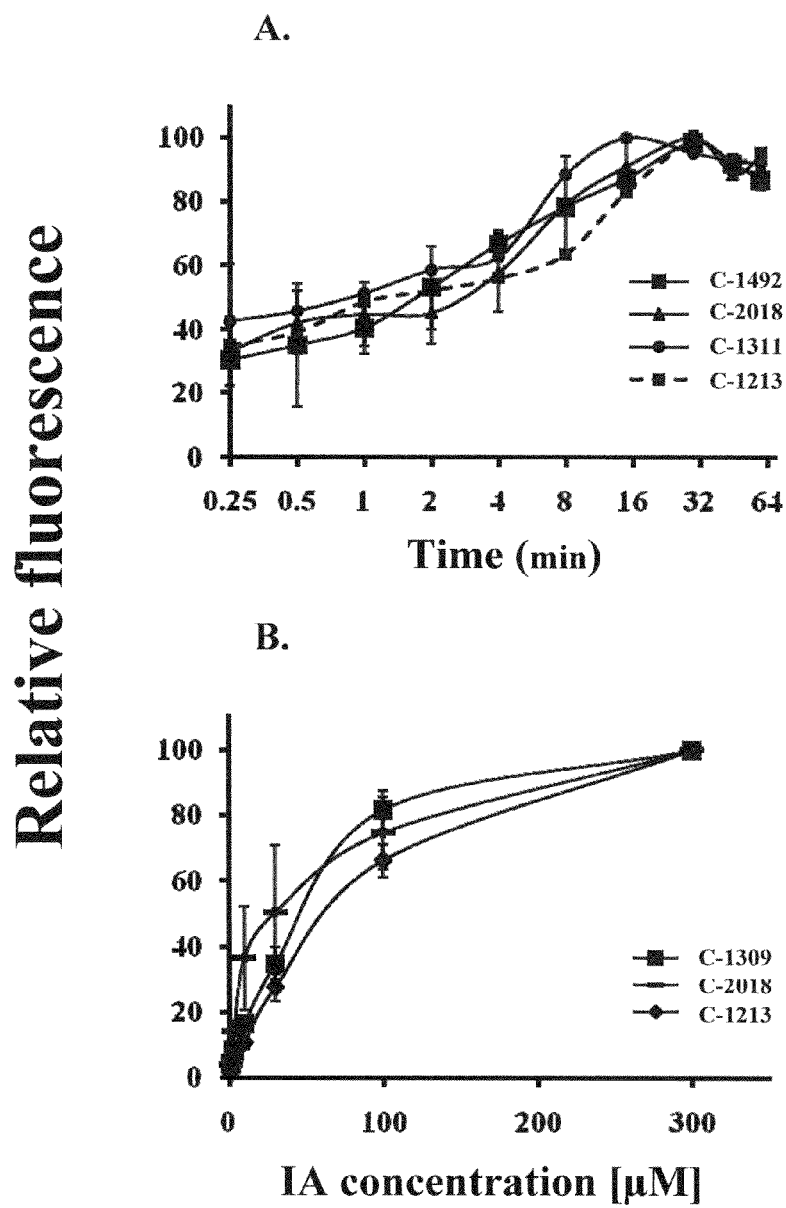
FIGS. 5A-5B show the time course and dose dependent accumulation of selected Group A and B IA derivatives in ABCG2-lacking CCRF-CEM cells. Cells were suspended in a 20 mM HEPES (pH 7.3)-buffered medium and incubated with 10 µM of selected Group A and B IA derivatives for increasing times up to 1 hr (A). Another portion of the cells was incubated for 1 hr in various concentrations of the selected IAs (B). Time and does dependent IA accumulation was than analyzed using flow cytometry. Results depicted are means±S.D obtained from at least 2 independent experiments.

In order to provide further evidence for the direct role of IA interaction with ABCG2 in the differential drug accumulation, a dose-dependent IA derivative accumulation was carried out (FIG. 5B). All IA derivatives studied displayed a comparable dose-dependent and saturable accumulation up to a concentration of 100 µM, thus supporting similar influx and accumulation kinetics (FIG. 5B).

Figure 8:
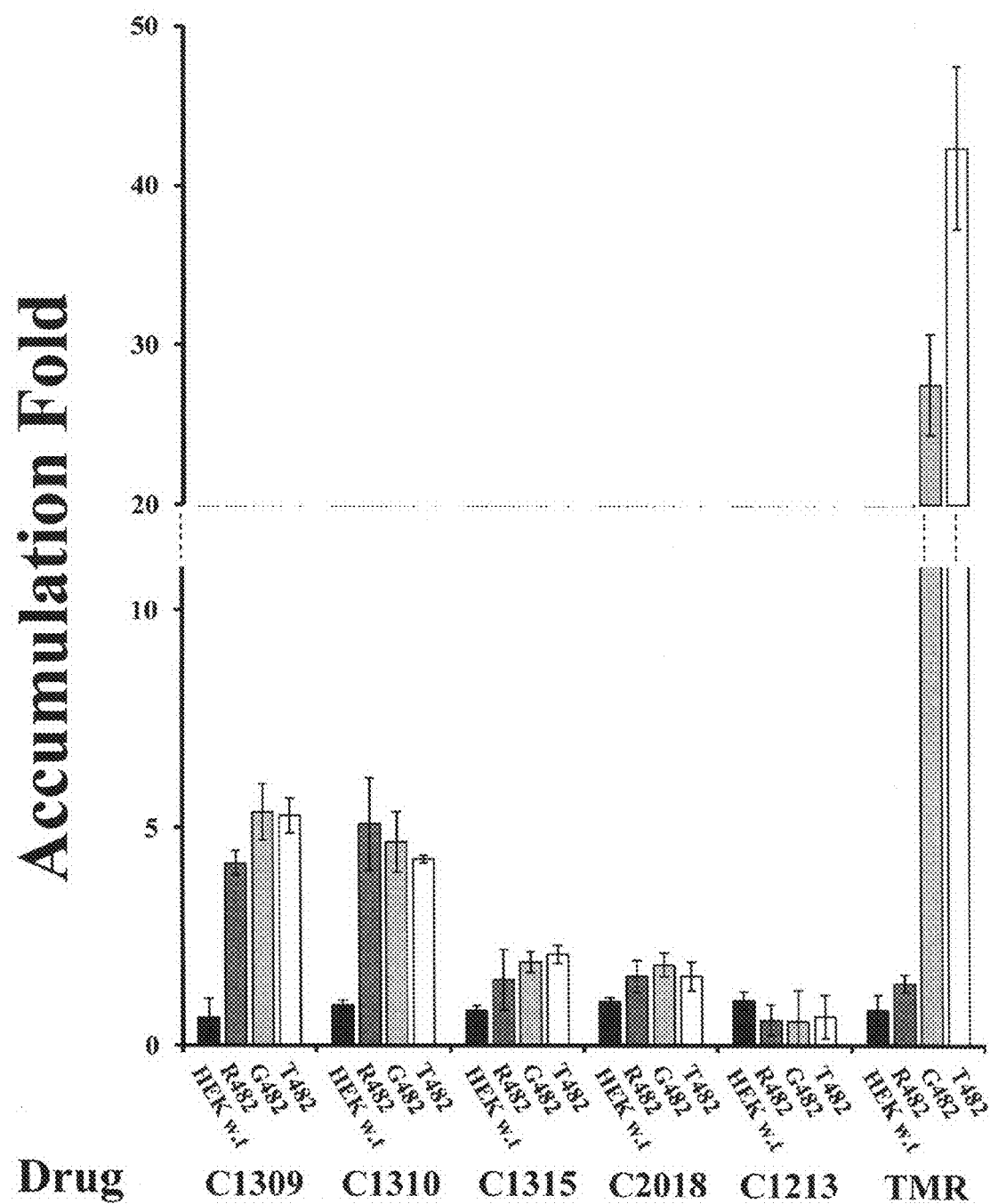
FIG. 8 shows IA derivative accumulation in HEK293 transfected cells expressing wild type R482/ABCG2 or mutant R482G/T ABCG2, in the presence or absence of fumitremorgin C. Cells were suspended in a 20 mM HEPES (pH 7.3)-buffered medium and incubated with 1 µM of selected Group A and B IA derivatives or 100 nM of Tetramethylrosamine at 37° C. for 1 hr in the presence and absence of 5 µM FTC. Results represent the mean FTC inducible accumulation fold (AF) of each IA derivatives in the wild type and mutant ABCG2 expressing cells. Mean values±S.D were obtained from at least 3 independent experiments.

In addition, mutant R482G and R482T ABCG2 do not alter IA substrate recognition. Previous reports have established that the R482G/T ABCG2 mutations can result in altered substrate specificity and augmented cellular drug resistance. Bram, E. E., et al., (2006) *Cancer Chemother Pharmacol* 58(6), 826-834. In order to determine whether or not these mutations alter IA substrate specificity and thereby facilitate the efflux of non-ABCG2 substrates of group B IA derivatives, a flow cytometric IA accumulation assay was employed using HEK293 cells stably transfected with w.t R482— as well as mutant G482- or T482-ABCG2 (FIG. 8). Group A IA derivatives C-1309 and C-1310 were efficiently extruded from both wild type R482 and mutant G482- and T482 ABCG2 overexpressing cells in a similar manner, but not from untransfected HEK293 cells (P-value=0.0001 and 0.00015, respectively; FIG. 8). By contrast, the group B IA derivative C-1213, which lacks a hydroxyl group, remained a non-substrate for both wild type and mutant G/T482 ABCG2, with statistically insignificant differences in AF values (P-value=0.22), compared to non-transfected HEK293 cells (FIG. 8). Likewise, lack of ABCG2-mediated efflux of the long tailed IA derivatives C-1315 and C-2018 was evident in all ABCG2 variants as well (P-value=0.12 and 0.1, respectively; FIG. 8). Moreover, TMR efflux is a distinct characteristic of mutant G/T482 but not wild type R482ABCG2. Indeed, mutant G482- and T482-ABCG2 displayed marked AF towards TMR, whereas wild type R482ABCG2 overexpressing cells displayed an AF of 1.4 that is comparable to the value (0.8 fold) obtained with untransfected HEK293 cells (FIG. 8).

EXAMPLE 3

Structural Analysis

Structural analysis of the IA derivatives showed that a hydroxyl group at one of the R1-R3 positions revolving the outer ring of the IA common structure mediates ABCG2-dependent drug efflux and resistance. Structural alignment of the various IA derivatives revealed a distinct difference between the two IA groups (Table I). Group A of ABCG2 substrates contains a hydroxyl group at position R1 of the common core structure, with the exception of C-1419 and C-1633, which alternatively possess a hydroxyl group at positions R2 and R3, respectively (Table I). All hydroxyl positions including R1, R2 and R3 are located around the outer proximal IA ring. In contrast, most of the IAs from group B of non-ABCG2 substrates lack the R1, R2, R3 hydroxyl group and contain various non-polar substitutions at these positions. Nonetheless, both C-1315 and C-2018 of group B, which possess a hydroxyl group at position R1, failed to display any significant interaction with ABCG2 (Table I).

Elongation of the IA side chain abolishes ABCG2-mediated IA efflux and drug resistance. C-1315 and C-2018 were found to be non-ABCG2 substrates despite the fact that they harbor a hydroxyl group at position R1. Close examination of the structure of these compounds reveals that both compounds possess the longest IA side chain (Table I). This exception to the general requirement of a hydroxyl group at the R1-R3 positions reflects a negative impact that the length of the IA side chain (i.e. tail) has on the ability of ABCG2 to recognize and expel these IA derivatives.

The length of the IA tail varies at 2 positions: the alkane length (n) and the distal branched Ra,b chain (Table I). C-1315 possesses a C=10 tail comprised of an alkane group of C=2 as well as an additional large branched Ra,b chain of C=8 (Table I). Additionally, C-2018 has a C=13 tail consisting mainly of a large (C=9) alkane group and a shorter branched Ra,b chain of C=4 (Table I).

The impact of IA tail length on the ability of ABCG2 to transport IA derivatives was assessed using an integrated parameter termed the relative ABCG2-IA interaction value (see Materials and Methods). This integrated parameter is comprised of the two established parameters described above: a) ABCG2-mediated drug efflux (AF) and b) drug resistance levels (RF). IA tail length was evaluated within several sets of IA derivatives differing only by the length of their branched side chain i.e Ra,b or the alkane length (n). The relative ABCG2-IA interaction parameter reflects the average of relative (%) RF and AF values for each IA, within the subset. Indeed, with all IA compounds studied, ABCG2 interaction with these compounds reveals an inverse correlation with IA branched tail group-Ra,b length (FIG. 6A). Elongation of Ra,b resulted in a significant decrease in the interaction of ABCG2 with IAs (P-value<0.03, FIG. 6A). Interestingly, elongation of the alkane tail (n) appears to have a lesser effect on ABCG2-mediated efflux and drug resistance. No significant decrease in ABCG2-IA interaction was observed for the pairs C-1584/C-1371 and C-1311/C-1335 (P-value=0.51 and 0.11, respectfully, FIG. 6B), both shifting from n=2 to n=3 alkane tail length (Table II). However, a further marked increase in tail length (n) in C-1492 (n=5) and C-2018 (n=9) (Table II) resulted in a statistically significant decrease in the ABCG2-IA interaction values (P-values=0.013 and 0.004, respectively, FIG. 6B).

In order to assess the relative contribution of the various structural determinants of IA derivatives to their ability to be extruded and therefore drug resistance via ABCG2, IA derivatives were divided into subgroups. Comparison was carried out within these subgroups. Each subgroup contained structurally identical IA derivatives that differ only at a single structural determinant. Within each subgroup, the effect of the specific structural change on ABCG2-IA interaction was evaluated using a combined parameter termed the relative ABCG2-IA interaction. This parameter was calculated by averaging the relative percent RF and AF values for each IA within the subgroup, thereby generating a combined mean±SE value.

Statistical Analyses: A non-paired student's T-test was used to examine the significance of the difference between two populations for a certain variable, and a 1-tailed Z-test was used to examine the significance of the difference between a population and a specific sample. A difference was considered significant if the P-value obtained was <0.05. In order to explore the possible mathematical relationship between two paired data sets of two variables, a non-linear curve fit analysis was applied (Microsoft® office Excel® 2007 ver. 12.0.6300.5000). $R^2$ values greater than 0.8 were considered sufficient.

Figure 7:
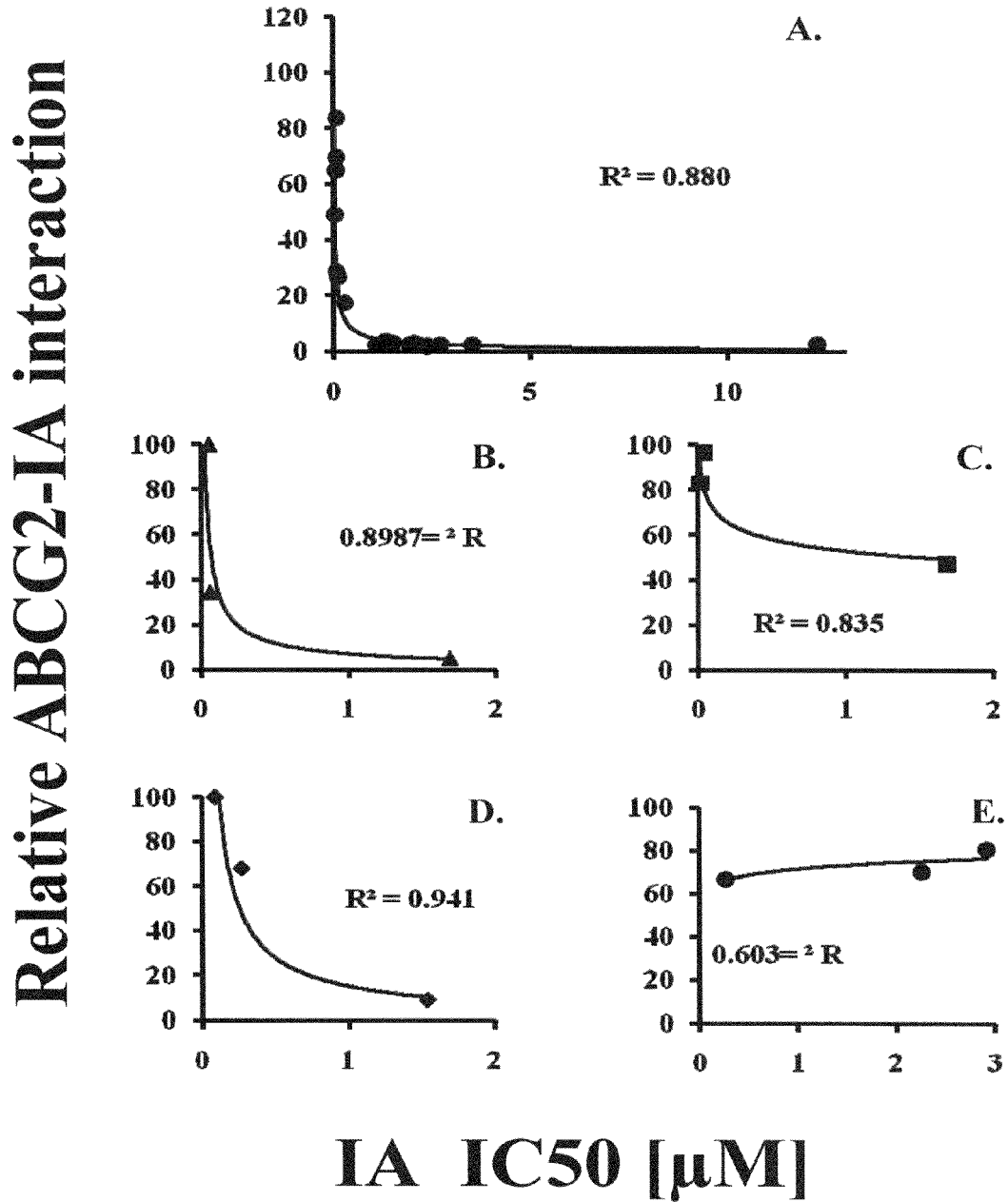
FIGS. 7A-7E show ABCG2-IA interaction correlations with IA toxicity. IA derivatives were divided into subgroups by the structural parameters that define ABCG2 interaction with IA derivatives. The integrated relative ABCG2-IA interaction value was then plotted against their IC50 values in ABCG2 lacking-sensitive A549 parental cells. Allometric regression curves and their R2 values for the subgroup data sets are presented; Subgroup A (16 IA derivatives: C-1584, C-1371, C-1309, C-1310, C-1335, C-1311, C-1379, C-1375, C-1558, C-1212, C-1554, C-1330, C-1176, C-1415, C-1503 and C-1213) consisted of all short side chained IA derivatives (n≦3, Ra,b≦Et), differing only by the presence or absence of the proximal ring OH— group (A). Subgroup B (3 IA derivatives: C-1309, C-1310, C-1315) differs only by the size of Ra,b (B). Subgroup C and D (3 IA derivatives each: C-1584, C-1371, C-1492 (C) and C-1335, C-1311, C-2018 (D)); both subgroups vary in (n) length. Subgroup E (3 IA derivatives: C-1311, C-1419 and C-1633), with alternative (R1-R3) positions for the ABCG2 interacting OH— group.

The relative ABCG2-IA interaction values correlates with IA derivative cytotoxicity. IA derivatives were subdivided into subsets based upon the above described ABCG2 interaction-defining parameters, including R1-hydroxyl (FIG. 7A), Ra,b size (FIG. 7B) and n-length (2 IA subsets, FIG. 7C-D). When plotting the relative ABCG2-IA interaction values of the various IAs versus their cytotoxicity (IC50), an inverse correlation was observed (FIG. 7A-D); the curve-fit derived function describing the relationship between these two parameters was found to be allometric (i.e power function). All subsets produced similar allometric regression curves with remarkable $R^2$ values of 0.88, 0.898, 0.835 and 0.941, respectively (FIGS. 7A-D). However, shifting the location of the ABCG2 interacting hydroxyl group from R1 to R2, or from R1 to R3 revealed a marked decrease in IA cytotoxicity (Table II) but did not significantly affect ABCG2-IA interaction (P-value>0.31, FIG. 6C). Hence, plotting the relative ABCG2-IA interaction of this subset of IA derivatives versus its cytotoxicity resulted in a dissimilar regression curve with a markedly decreased $R^2$ value (0.603) (FIG. 7E).

Although the invention has been described with reference to the examples provided above, it should be understood that various modifications can be made by those skilled in the art without departing from the invention. Accordingly, the invention is set out in the following claims.

All references cited herein are incorporated in their entirety.

What is claimed is:

1. A method of testing a compound for activity against cancer, comprising testing a compound of the formula

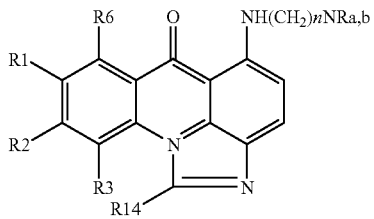

Wherein:
R1 is selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R2, R3 and R6 are, independently, selected from the group consisting of hydrogen, halogen, hydroxy, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R14, Ra and Rb are, independently, selected from the group consisting of hydrogen, $C_1$ to $C_{12}$ alkyl and $C_1$ to $C_{12}$ substituted alkyl; and n is 6 to 30;

wherein said cancer is selected from leukemia, lung cancer and colorectal cancer.

2. The method of claim 1, wherein R1 is selected from the group consisting of hydrogen, $C_1$ to $C_6$ alkyl and $C_1$ to $C_6$ alkoxy; and R2, R3 and R6 are, independently, selected from the group consisting of hydrogen, hydroxy, $C_1$ to $C_6$ alkyl and $C_1$ to $C_6$ alkoxy.

3. The method of claim 2, wherein R1 is selected from the group consisting of hydrogen, $C_1$ to $C_3$ alkyl and methoxy; and R2 and R3 are, independently, selected from the group consisting of hydrogen, hydroxy, $C_1$ to $C_3$ alkyl and methoxy.

4. The method of claim 2, wherein R6 is selected from the group consisting of hydrogen and methoxy.

5. The method of claim 1, wherein R14, Ra and Rb are, independently, selected from the group consisting of hydrogen and $C_1$ to $C_3$ alkyl.

6. The method of claim 1, wherein said cancer is leukemia.

7. The method of claim 1, wherein said cancer is lung cancer.

8. The method of claim 7, wherein said lung cancer is non-small cell.

9. The method of claim 1, wherein said cancer is colorectal cancer.

10. A method of improving the status of a subject with cancer, comprising administering to said subject a compound of the formula

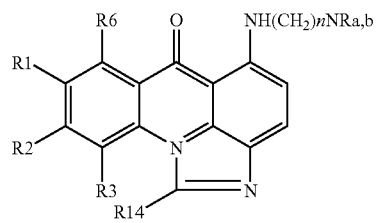

wherein:
R1 is selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R2, R3 and R6 are, independently, selected from the group consisting of hydrogen, halogen, hydroxy, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R14, Ra and Rb are, independently, selected from the group consisting of hydrogen, $C_1$ to $C_{12}$ alkyl and $C_1$ to $C_{12}$ substituted alkyl; and n is 6 to 30;

wherein said cancer is selected from leukemia, lung cancer and colorectal cancer.

11. The method of claim 10, wherein R1 is selected from the group consisting of hydrogen, $C_1$ to $C_6$ alkyl and $C_1$ to $C_6$ alkoxy; and R2, R3 and R6 are, independently, selected from the group consisting of hydrogen, hydroxy, $C_1$ to $C_6$ alkyl and $C_1$ to $C_6$ alkoxy.

12. The method of claim 11, wherein R1 is selected from the group consisting of hydrogen, $C_1$ to $C_3$ alkyl and methoxy; and R2 and R3 are, independently, selected from the group consisting of hydrogen, hydroxy, $C_1$ to $C_3$ alkyl and methoxy.

13. The method of claim 11, wherein R6 is selected from the group consisting of hydrogen and methoxy.

14. The method of claim 10, wherein R14, Ra and Rb are, independently, selected from the group consisting of hydrogen and $C_1$ to $C_3$ alkyl.

15. The method of claim 10, wherein said cancer is leukemia.

16. The method of claim 10, wherein said cancer is lung cancer.

17. The method of claim 16, wherein said lung cancer is non-small cell.

18. The method of claim 10, wherein said cancer is colorectal cancer.

19. A compound of the formula:

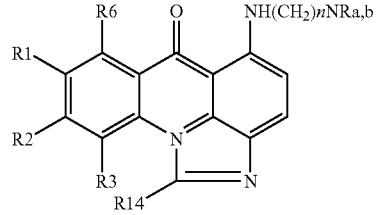

wherein:
R1 is selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;
R2, R3 and R6 are, independently, selected from the group consisting of hydrogen, halogen, hydroxy, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;
R14, Ra and Rb are, independently, selected from the group consisting of hydrogen, $C_1$ to $C_{12}$ alkyl and $C_1$ to $C_{12}$ substituted alkyl; and
n is 6 to 30.

20. The compound of claim 19, wherein R1 is selected from the group consisting of hydrogen, $C_1$ to $C_6$ alkyl and $C_1$ to $C_6$ alkoxy; and R2, R3 and R6 are, independently, selected from the group consisting of hydrogen, hydroxy, $C_1$ to $C_6$ alkyl and $C_1$ to $C_6$ alkoxy.

21. The compound of claim 20, wherein R1 is selected from the group consisting of hydrogen, $C_1$ to $C_3$ alkyl and methoxy; and R2 and R3 are, independently, selected from the group consisting of hydrogen, hydroxy, $C_1$ to $C_3$ alkyl and methoxy.

22. The compound of claim 20, wherein R6 is selected from the group consisting of hydrogen and methoxy.

23. The compound of claim 19, wherein R14, Ra and Rb are, independently, selected from the group consisting of hydrogen and $C_1$ to $C_3$ alkyl.

24. The method of claim 1, wherein n is greater than 6.
25. The method of claim 10, wherein n is greater than 6.
26. The compound of claim 19, wherein n is greater than 6.
27. A method of testing a compound for activity against cancer, comprising testing a compound of the formula

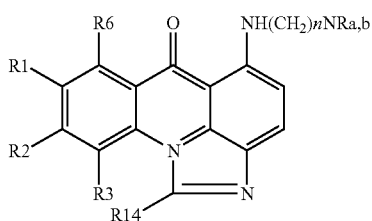

Wherein:
R1, R2 and R3 are, independently, selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ acyl, $C_1$ to $C_6$ acyloxy, nitro, carboxy, carbamoyl, carboxamide, cyano and thiol;
R6 is selected from the group consisting of hydrogen, halogen, hydroxy, $C_1$ to $C_6$ alkyl, $C_1$ to $C_6$ substituted alkyl, oxo, amino, protected amino, (monosubstituted) amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;
R14, Ra and Rb are, independently, selected from the group consisting of hydrogen, $C_1$ to $C_{12}$ alkyl and $C_1$ to $C_{12}$ substituted alkyl; and
n is 1 to 30;
provided that Ra and Rb together include more than 4 carbon atoms;
wherein said cancer is selected from leukemia, lung cancer and colorectal cancer.

28. The method of claim 27, wherein Ra and Rb together include more than 5 carbon atoms.

29. A method of improving the status of a subject with cancer, comprising administering to said subject a compound of the formula

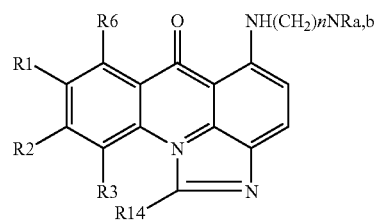

Wherein:
R1, R2 and R3 are, independently, selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ acyl, $C_1$ to $C_6$ acyloxy, nitro, carboxy, carbamoyl, carboxamide, cyano and thiol;
R6 is selected from the group consisting of hydrogen, halogen, hydroxy, $C_1$ to $C_6$ alkyl, $C_1$ to $C_6$ substituted alkyl, oxo, amino, protected amino, (monosubstituted) amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;
R14, Ra and Rb are, independently, selected from the group consisting of hydrogen, $C_1$ to $C_{12}$ alkyl and $C_1$ to $C_{12}$ substituted alkyl; and
n is 1 to 30;
provided that Ra and Rb together include more than 4 carbon atoms;
wherein said cancer is selected from leukemia, lung cancer and colorectal cancer.

30. The method of claim 29, wherein Ra and Rb together include more than 5 carbon atoms.

31. A compound of the formula:

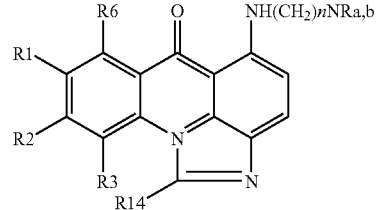

Wherein:
R1, R2 and R3 are, independently, selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ acyl, $C_1$ to $C_6$ acyloxy, nitro, carboxy, carbamoyl, carboxamide, cyano and thiol;
R6 is selected from the group consisting of hydrogen, halogen, hydroxy, $C_1$ to $C_6$ alkyl, $C_1$ to $C_6$ substituted alkyl, oxo, amino, protected amino, (monosubstituted) amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R14, Ra and Rb are, independently, selected from the group consisting of hydrogen, $C_1$ to $C_{12}$ alkyl and $C_1$ to $C_{12}$ substituted alkyl; and n is 1 to 30;

provided that Ra and Rb together include more than 4 carbon atoms.

32. The compound of claim 31, wherein Ra and Rb together include more than 5 carbon atoms.

33. A method of testing a compound for activity against cancer, comprising testing a compound of the formula

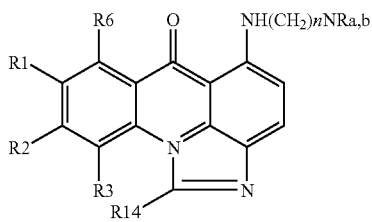

Wherein:

R1, R2 and R3 are, independently, selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R6 is selected from the group consisting of hydrogen, halogen, hydroxy, $C_1$ to $C_6$ alkyl, $C_1$ to $C_6$ substituted alkyl, oxo, amino, protected amino, (monosubstituted) amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R14, Ra and Rb are, independently, selected from the group consisting of hydrogen, $C_1$ to $C_{12}$ alkyl and $C_1$ to $C_{12}$ substituted alkyl; and n is 1 to 30;

provided that Ra and Rb together include more than 4 carbon atoms;

wherein said cancer is selected from lung cancer and colorectal cancer.

34. The method of claim 33, wherein Ra and Rb together include more than 5 carbon atoms.

35. A method of improving the status of a subject with cancer, comprising administering to said subject a compound of the formula

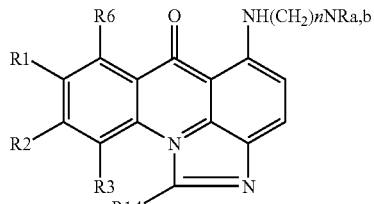

Wherein:

R1, R2 and R3 are, independently, selected from the group consisting of hydrogen, halogen, $C_1$ to $C_6$ alkyl, $C_1$ to $C_6$ substituted alkyl, oxo, amino, protected amino, (monosubstituted)amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R6 is selected from the group consisting of hydrogen, halogen, hydroxy, $C_1$ to $C_6$ alkyl, $C_1$ to $C_6$ substituted alkyl, oxo, amino, protected amino, (monosubstituted) amino, (disubstituted)amino, $C_1$ to $C_6$ alkoxy, $C_1$ to $C_6$ substituted alkoxy, $C_1$ to $C_6$ acyl, $C_1$ to $C_6$ acyloxy, nitro, carboxy, carbamoyl, carboxamide, cyano and thiol;

R14, Ra and Rb are, independently, selected from the group consisting of hydrogen, $C_1$ to $C_{12}$ alkyl and $C_1$ to $C_{12}$ substituted alkyl; and n is 1 to 30;

provided that Ra and Rb together include more than 4 carbon atoms;

wherein said cancer is selected from lung cancer and colorectal cancer.

36. The method of claim 35, wherein Ra and Rb together include more than 5 carbon atoms.

* * * * *